(12) United States Patent
Vidlund

(10) Patent No.: US 11,925,339 B2
(45) Date of Patent: *Mar. 12, 2024

(54) BLOOD VESSEL ACCESS AND CLOSURE DEVICES AND RELATED METHODS OF USE

(71) Applicant: J.D. Franco & Co., LLC, Plano, TX (US)

(72) Inventor: Robert Vidlund, Forest Lake, MN (US)

(73) Assignee: J.D. Franco & Co., LLC, Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,412

(22) Filed: Nov. 10, 2022

(65) Prior Publication Data

US 2023/0149004 A1 May 18, 2023

Related U.S. Application Data

(63) Continuation of application No. 16/480,549, filed as application No. PCT/US2018/014766 on Jan. 23, 2018, now Pat. No. 11,529,130.

(Continued)

(51) Int. Cl.
*A61B 17/12* (2006.01)
*A61B 17/00* (2006.01)
*A61B 17/34* (2006.01)

(52) U.S. Cl.
CPC .......... *A61B 17/0057* (2013.01); *A61B 17/12* (2013.01); *A61B 17/3415* (2013.01);
(Continued)

(58) Field of Classification Search
CPC .. A61B 2017/00606; A61B 2017/0417; A61B 2017/0419; A61B 2017/0496;
(Continued)

(56) References Cited

U.S. PATENT DOCUMENTS 2,690,595 A 10/1954 Raiche
3,367,101 A 2/1968 Harold et al.
(Continued)

FOREIGN PATENT DOCUMENTS

EP 2495006 A1 9/2012
WO 9852939 A1 11/1998
(Continued)

OTHER PUBLICATIONS

Altinbas, N.K. et al., "Effect of Carotid Artery Stenting on Ophthalmic Artery Flow Patterns," Journal of Ultrasound Medicine, 2014; 33: pp. 629-638.
(Continued)

*Primary Examiner* — Majid Jamialahmadi
(74) *Attorney, Agent, or Firm* — Bookoff McAndrews, PLLC

(57) ABSTRACT

A medical device may include an outer assembly having a first shaft, a first lumen extending through the first shaft, and an atraumatic first tip removably coupled to a distal end of the first shaft; an inner assembly configured to extend through the first lumen of the outer assembly, the inner assembly including a second shaft, a second lumen extending through the second shaft, and a second tip removably coupled to a distal end of the second shaft, the second tip being configured to pierce tissue; and a plug assembly configured to extend through the second lumen of the inner assembly, the plug assembly including a third shaft and a plug removably coupled to a distal end of the third shaft.

19 Claims, 26 Drawing Sheets

Related U.S. Application Data

(60) Provisional application No. 62/525,839, filed on Jun. 28, 2017.

(52) U.S. Cl.
CPC .................. *A61B 17/3421* (2013.01); *A61B 2017/00473* (2013.01); *A61B 2017/00637* (2013.01); *A61B 2017/3454* (2013.01)

(58) Field of Classification Search
CPC ........... A61B 2017/00575; A61B 2017/00637; A61B 2017/00641; A61B 17/0057; A61B 17/3421; A61B 17/3415; A61B 17/12; A61M 2039/0258
See application file for complete search history.

(56) References Cited

U.S. PATENT DOCUMENTS

| | | | |
|---|---|---|---|
| 3,435,826 A | 4/1969 | Fogarty | |
| 3,970,090 A | 7/1976 | Loiacono | |
| 4,224,929 A | 9/1980 | Furihata | |
| 4,403,612 A | 9/1983 | Fogarty | |
| 4,445,897 A | 5/1984 | Ekbladh et al. | |
| 4,794,931 A | 1/1989 | Yock | |
| 4,857,045 A | 8/1989 | Rydell | |
| 4,886,061 A | 12/1989 | Fischell et al. | |
| 4,894,051 A | 1/1990 | Shiber | |
| 4,898,575 A | 2/1990 | Fischell et al. | |
| 4,926,858 A | 5/1990 | Gifford, III et al. | |
| 4,936,835 A | 6/1990 | Haaga | |
| 4,950,277 A | 8/1990 | Farr | |
| 4,957,482 A | 9/1990 | Shiber | |
| 4,979,939 A | 12/1990 | Shiber | |
| 4,986,807 A | 1/1991 | Farr | |
| 5,000,185 A | 3/1991 | Yock | |
| 5,000,734 A | 3/1991 | Boussignac et al. | |
| 5,007,896 A | 4/1991 | Shiber | |
| 5,019,088 A | 5/1991 | Farr | |
| 5,024,651 A | 6/1991 | Shiber | |
| 5,026,384 A | 6/1991 | Farr et al. | |
| 5,087,265 A | 2/1992 | Summers | |
| 5,100,425 A | 3/1992 | Fischell et al. | |
| 5,135,531 A | 8/1992 | Shiber | |
| 5,176,693 A | 1/1993 | Pannek, Jr. | |
| 5,292,332 A | 3/1994 | Lee | |
| 5,313,949 A | 5/1994 | Yock | |
| 5,314,438 A | 5/1994 | Shturman | |
| 5,318,576 A | 6/1994 | Plassche, Jr. et al. | |
| 5,336,234 A | 8/1994 | Vigil et al. | |
| 5,366,464 A | 11/1994 | Belknap | |
| 5,395,311 A | 3/1995 | Andrews | |
| 5,402,790 A | 4/1995 | Jang et al. | |
| 5,409,454 A | 4/1995 | Fischell et al. | |
| 5,415,634 A | 5/1995 | Glynn et al. | |
| 5,419,761 A | 5/1995 | Narayanan et al. | |
| 5,507,292 A | 4/1996 | Jang et al. | |
| 5,554,119 A | 9/1996 | Harrison et al. | |
| 5,709,701 A | 1/1998 | Parodi | |
| 5,820,595 A | 10/1998 | Parodi | |
| 5,897,567 A | 4/1999 | Ressemann et al. | |
| 5,951,514 A | 9/1999 | Sahota | |
| 5,972,019 A | 10/1999 | Engelson et al. | |
| 6,010,522 A | 1/2000 | Barbut et al. | |
| 6,146,370 A | 11/2000 | Barbut | |
| 6,206,868 B1 | 3/2001 | Parodi | |
| 6,302,908 B1 | 10/2001 | Parodi | |
| 6,336,933 B1 | 1/2002 | Parodi | |
| 6,344,054 B1 | 2/2002 | Parodi | |
| 6,413,235 B1 | 7/2002 | Parodi | |
| 6,423,032 B2 | 7/2002 | Parodi | |
| 6,494,890 B1 | 12/2002 | Shturman et al. | |
| 6,540,712 B1 | 4/2003 | Parodi et al. | |
| 6,595,980 B1 | 7/2003 | Barbut | |
| 6,623,471 B1 | 9/2003 | Barbut | |
| 6,626,861 B1 | 9/2003 | Hart et al. | |
| 6,641,573 B1 | 11/2003 | Parodi | |
| 6,645,222 B1 | 11/2003 | Parodi et al. | |
| 6,824,558 B2 | 11/2004 | Parodi | |
| 6,827,726 B2 | 12/2004 | Parodi | |
| 6,837,881 B1 | 1/2005 | Barbut | |
| 6,855,162 B2 | 2/2005 | Parodi | |
| 6,902,540 B2 | 6/2005 | Dorros et al. | |
| 6,905,490 B2 | 6/2005 | Parodi | |
| 6,908,474 B2 | 6/2005 | Hogendijk et al. | |
| 6,929,634 B2 | 8/2005 | Dorros et al. | |
| 6,936,053 B1 | 8/2005 | Weiss | |
| 6,936,060 B2 | 8/2005 | Hogendijk et al. | |
| 6,974,469 B2 | 12/2005 | Broome et al. | |
| 7,195,611 B1 | 3/2007 | Simpson et al. | |
| 7,214,201 B2 | 5/2007 | Burmeister et al. | |
| 7,235,095 B2 | 6/2007 | Haverkost et al. | |
| 7,309,334 B2 | 12/2007 | Hoffmann | |
| 7,384,411 B1 | 6/2008 | Condado | |
| 7,604,612 B2 | 10/2009 | Ressemann et al. | |
| 7,806,906 B2 | 10/2010 | Michael | |
| 7,867,273 B2 | 1/2011 | Pappas et al. | |
| 7,901,445 B2 | 3/2011 | Wallace et al. | |
| 7,918,800 B1 | 4/2011 | Brown et al. | |
| 7,927,347 B2 | 4/2011 | Hogendijk et al. | |
| 8,123,779 B2 | 2/2012 | Demond et al. | |
| 8,157,760 B2 | 4/2012 | Criado et al. | |
| 8,267,956 B2 | 9/2012 | Salahieh et al. | |
| 8,353,850 B2 | 1/2013 | Ressemann et al. | |
| 8,409,237 B2 | 4/2013 | Galdonik et al. | |
| 8,414,516 B2 | 4/2013 | Chang | |
| 8,439,937 B2 | 5/2013 | Montague et al. | |
| 8,545,432 B2 | 10/2013 | Renati et al. | |
| 8,834,404 B2 | 9/2014 | Beaudin | |
| 8,852,226 B2 | 10/2014 | Gilson et al. | |
| 8,863,631 B1 | 10/2014 | Janardhan et al. | |
| 9,078,682 B2 | 7/2015 | Lenker et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 9,987,164 B2 | 6/2018 | Calhoun et al. | |
| 10,195,077 B2 | 2/2019 | Calhoun et al. | |
| 10,265,085 B2 | 4/2019 | Zaidat | |
| 10,342,699 B2 | 7/2019 | Calhoun et al. | |
| 2001/0001114 A1 | 5/2001 | Tsugita et al. | |
| 2002/0038103 A1 | 3/2002 | Estrada et al. | |
| 2002/0077656 A1 | 6/2002 | Ginn et al. | |
| 2002/0077658 A1 | 6/2002 | Ginn | |
| 2002/0087128 A1 | 7/2002 | Paques et al. | |
| 2002/0143291 A1 | 10/2002 | Slater | |
| 2002/0151922 A1 | 10/2002 | Hogendijk et al. | |
| 2002/0165573 A1 | 11/2002 | Barbut | |
| 2003/0023200 A1 | 1/2003 | Barbut et al. | |
| 2003/0023227 A1 | 1/2003 | Zadno-Azizi et al. | |
| 2003/0199802 A1 | 10/2003 | Barbut | |
| 2003/0199819 A1 | 10/2003 | Beck | |
| 2003/0203958 A1 | 10/2003 | Kunz et al. | |
| 2005/0149117 A1 | 7/2005 | Khosravi et al. | |
| 2006/0089618 A1 | 4/2006 | McFerran et al. | |
| 2006/0136022 A1 | 6/2006 | Wong et al. | |
| 2006/0259132 A1 | 11/2006 | Schaffer et al. | |
| 2006/0276838 A1 | 12/2006 | Wensel et al. | |
| 2007/0026035 A1 | 2/2007 | Burke et al. | |
| 2008/0027519 A1 | 1/2008 | Guerrero | |
| 2008/0243229 A1 | 10/2008 | Wallace et al. | |
| 2009/0018455 A1 | 1/2009 | Chang | |
| 2009/0024072 A1 | 1/2009 | Criado et al. | |
| 2009/0030323 A1 | 1/2009 | Fawzi et al. | |
| 2009/0221961 A1 | 9/2009 | Tal et al. | |
| 2010/0076365 A1 | 3/2010 | Riina et al. | |
| 2010/0100045 A1 | 4/2010 | Pravongviengkham et al. | |
| 2010/0125244 A1 | 5/2010 | McAndrew | |
| 2010/0234884 A1 | 9/2010 | Lafontaine et al. | |
| 2011/0082495 A1* | 4/2011 | Ruiz .................. A61B 17/0057 |
| | | | 606/213 |
| 2011/0143993 A1 | 6/2011 | Langer et al. | |
| 2011/0152683 A1 | 6/2011 | Gerrans et al. | |
| 2011/0152998 A1 | 6/2011 | Berez et al. | |
| 2011/0160762 A1 | 6/2011 | Hogendijk et al. | |

(56) References Cited

U.S. PATENT DOCUMENTS

| | | |
|---|---|---|
| 2011/0274748 A1 | 11/2011 | Robinson et al. |
| 2012/0046679 A1 | 2/2012 | Patel et al. |
| 2012/0078287 A1 | 3/2012 | Barbut |
| 2012/0101510 A1 | 4/2012 | Lenker et al. |
| 2013/0035628 A1 | 2/2013 | Garrison et al. |
| 2013/0197621 A1 | 8/2013 | Ryan et al. |
| 2013/0281788 A1 | 10/2013 | Garrison |
| 2014/0154246 A1 | 6/2014 | Robinson et al. |
| 2014/0222066 A1 | 8/2014 | Tegels |
| 2015/0025562 A1 | 1/2015 | Dinh et al. |
| 2015/0032121 A1 | 1/2015 | Janardhan et al. |
| 2015/0065804 A1 | 3/2015 | Kleyman |
| 2015/0231378 A1 | 8/2015 | Pepper |
| 2015/0272732 A1 | 10/2015 | Tilson et al. |
| 2015/0313607 A1 | 11/2015 | Zhadkevich |
| 2015/0359547 A1 | 12/2015 | Vale et al. |
| 2015/0359549 A1 | 12/2015 | Lenker et al. |
| 2015/0366580 A1 | 12/2015 | Lenihan et al. |
| 2016/0166754 A1 | 6/2016 | Kassab et al. |
| 2016/0213893 A1 | 7/2016 | Franklin |
| 2016/0279385 A1 | 9/2016 | Katsurada et al. |
| 2016/0317328 A1 | 11/2016 | Berez et al. |
| 2017/0164963 A1 | 6/2017 | Goyal |
| 2017/0239453 A1 | 8/2017 | Kawakita et al. |
| 2017/0274179 A1 | 9/2017 | Sullivan et al. |
| 2017/0326001 A1 | 11/2017 | Franco et al. |
| 2017/0348120 A1 | 12/2017 | Calhoun et al. |
| 2018/0132876 A1 | 5/2018 | Zaidat |
| 2019/0192164 A1 | 6/2019 | Parekh et al. |
| 2019/0388112 A1 | 12/2019 | Nguyen et al. |

FOREIGN PATENT DOCUMENTS

| | | |
|---|---|---|
| WO | 9853761 A1 | 12/1998 |
| WO | 0054673 A1 | 9/2000 |
| WO | 03018085 A2 | 3/2003 |
| WO | 2007103464 A2 | 9/2007 |
| WO | 2011156782 A1 | 12/2011 |
| WO | 2012162651 A1 | 11/2012 |
| WO | 2014022866 A1 | 2/2014 |
| WO | 2016109586 A1 | 7/2016 |
| WO | 2016149653 A2 | 9/2016 |
| WO | 2017156333 A1 | 9/2017 |
| WO | 2018053121 A1 | 3/2018 |
| WO | 2018106858 A1 | 6/2018 |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Aurboonyawat et al., "Indirect Carotid-Cavernous Sinus Fistulas Treated by Transvenous Approach Through the Superior Ophthalmic Vein: A Case Report and Technical Note," Siriraj Med. J., vol. 59, pp. 191-194, 2007.

Bird, B. et al., "Anatomy, Head and Neck, Ophthalmic Arteries," NCBI Bookshelf, a service of the National Library of Medicine, National Institutes of Health, Oct. 27, 2018, 5 pages. www.ncbi.nlm.nih.gov/books/NBK482317/.

Examination Report No. 2 for AU Application No. 2013296195, dated Jun. 27, 2017 (6 pages).

Extended European Search Report for EP 18745369.1, dated Nov. 18, 2020 (6 pages).

Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.

Hayreh et al., "Ocular Arterial Occlusive Disorders and Carotid Artery Disease," American Academy of Ophthalmology, 2017; vol. 1, No. 1: pp. 12-18.

Hayreh et al., "The Ophthalmic Artery," Brit. J. Ophthal., 1962; 46, 65: pp. 65-98.

Hayreh, S.S., "The Ophthalmic Artery III. Branches," British Journal of Ophthalmology, 1962, 46, pp. 212-247.

Wang, G. et al., "Reversal of Ischemic Retinopathy Following Balloon Angioplasty of a Stenotic Ophthalmic Artery." Journal of Neuro-Ophthalmology 30.3, 2010, pp. 228-230.

International Search Report and Written Opinion for corresponding PCT/US2013/053670, dated Dec. 26, 2013 (16 pp.).

International Search Report and Written Opinion for International Application No. PCT/US2017/0051551, dated Dec. 15, 2017 (14 pages).

International Search Report and Written Opinion for International Application No. PCT/US2017/0052901, dated Dec. 8, 2017 (9 pages).

International Search Report and Written Opinion for International Application No. PCT/US2018/031229, dated Jul. 27, 2018 (19 pages).

International Search Report and Written Opinion for International Application No. PCT/US2019/068758, dated May 29, 2020 (16 pages).

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kleintjes, "Forehead anatomy: Arterial variations and venous link of the midline forehead flap," Journal of Plastic, Reconstructive & Aesthetic Surgery, vol. 60, Issue 6, pp. 593-606, 2007.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Loh, K. et al., "Prevention and management of vision loss relating to facial filler injections." Singapore Medical Journal, 2016; 57(8): 438-443.

Mazur et al., Catheterization and Cardiovascular Diagnosis, vol. 31, Issue 1, Abstract (1994).

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Notice of Allowance for KR 20157005602, dated Sep. 25, 2017 (3 pages).

Paques, M. et al., "Superselective ophthalmic artery fibrinolytic therapy for the treatment of central retinal vein occlusion." British Journal of Ophthalmology, 2000, 84: 1387-1391.

Schumacher, M. et al., "Intra-arterial fibrinolytic therapy in central retinal artery occlusion," Neuroradiology (1993) 35: pp. 600-605.

Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.

Tan, P.L. et al., "AMD and the alternative complement pathway: genetics and functional implications," Human Genomics, 2016, 10:23, 13 pages.

(56) References Cited

OTHER PUBLICATIONS

Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.
Written Opinion and International Search Report dated Mar. 29, 2018, of International Patent Application No. PCT/US2018/14766. (7 pages).
Xu, H. et al., "Targeting the complement system for the management of retinal inflammatory and degenerative diseases," European Journal of Pharmacology, 2016, 787, pp. 94-104.
Yamane, T. et al., "The technique of ophthalmic arterial infusion therapy for patients with intraocular retinoblastoma," International Journal of Clinical Oncology, Apr. 2004; vol. 9, Issue 2, pp. 69-73.
Zeumer, H. et al., "Local intra-arterial fibrinolytic therapy in patients with stroke: urokinase versus recombinant tissue plagminogen activator (r-TPA)," Neuroradiology, 1993; 35: pp. 159-162.
Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.
Zipfel, P.F., et al., "The Role of Complement in AMD," Inflammation and Retinal Disease: Complement Biology and Pathology, Advances in Experimental Medicine and Biology, 2010, 703, pp. 9-24.

\* cited by examiner

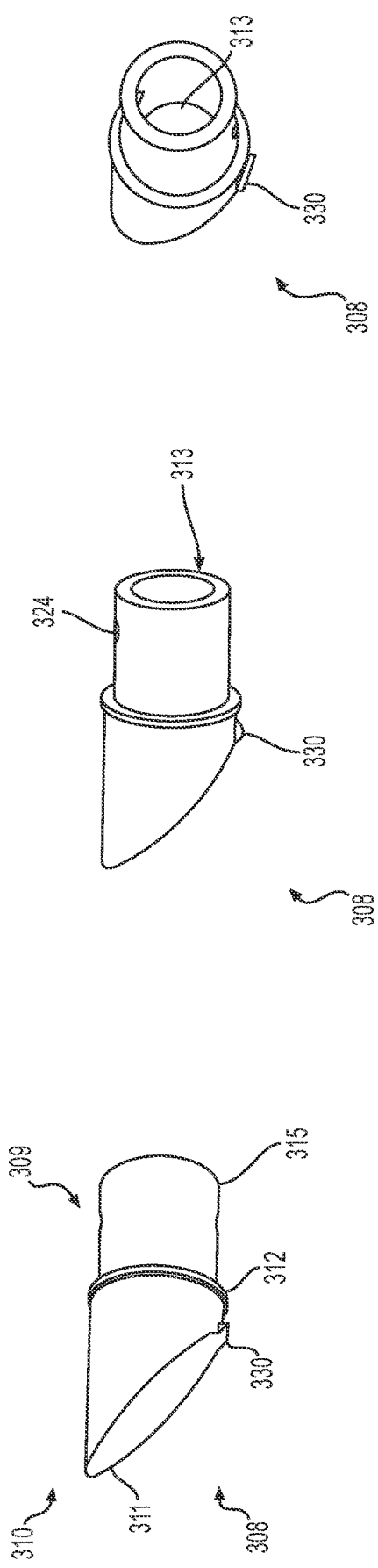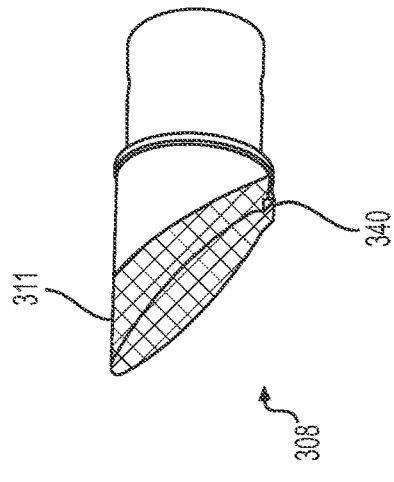

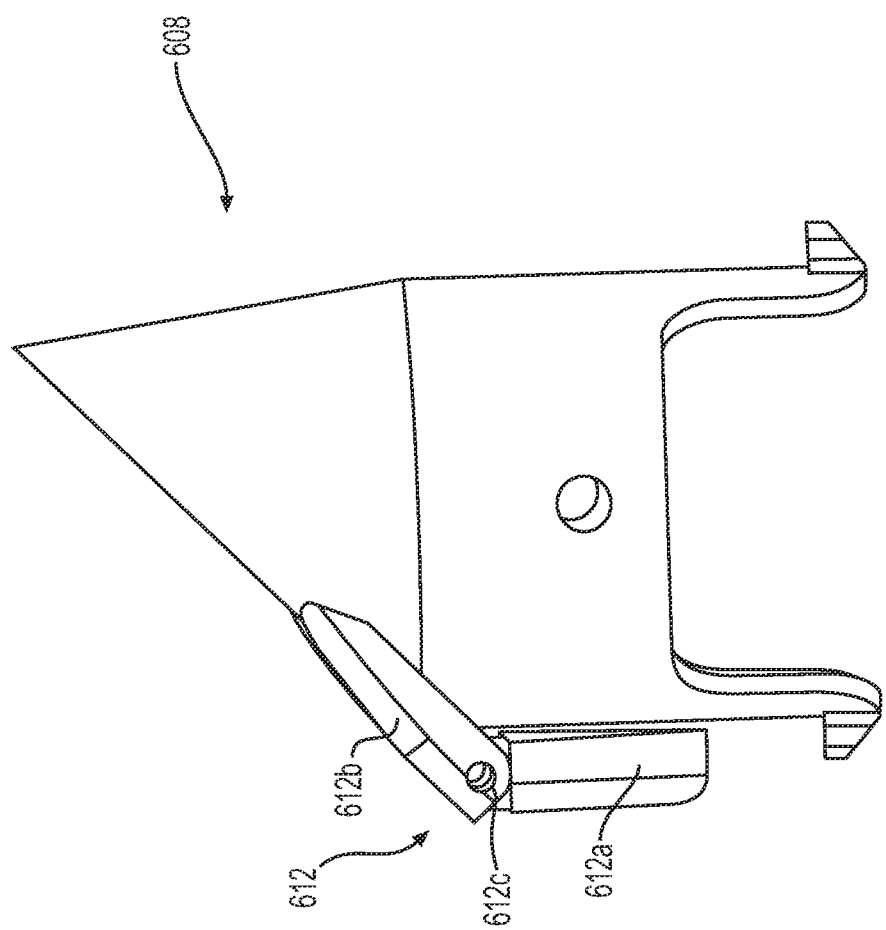

BLOOD VESSEL ACCESS AND CLOSURE DEVICES AND RELATED METHODS OF USE

CROSS-REFERENCE TO RELATED APPLICATIONS

This patent application is a continuation application of U.S. application Ser. No. 16/480,549, filed on Jul. 24, 2019, which is a national phase entry under 35 U.S.C. § 371 of International PCT Patent Application No. PCT/US2018/014766, filed Jan. 23, 2018, which claims the benefits of priority under 35 U.S.C. § 119 to U.S. Provisional Application No. 62/450,257, filed Jan. 25, 2017, and to U.S. Provisional Application No. 62/525,839, filed Jun. 28, 2017, the entireties of each of which are incorporated herein by reference.

TECHNICAL FIELD

Embodiments of the present disclosure relate to devices for accessing a blood vessel by creating an opening through a wall of the blood vessel, and for subsequently closing the opening, and related methods of use.

BACKGROUND

Various mechanisms are available for accessing a blood vessel in order to perform a medical procedure inside the blood vessel or other part of the cardiovascular system. However, many conventional techniques position a sheath or other member within the blood vessel, restricting the field of view within the vessel, and restricting the ability to navigate tools both proximally and distally of the point of insertion. Additionally, procedure times for conventional techniques may be higher than optimal.

SUMMARY

In one aspect, the disclosure is directed to a medical device including an outer assembly having a first shaft, a first lumen extending through the first shaft, and an atraumatic first tip removably coupled to a distal end of the first shaft; an inner assembly configured to extend through the first lumen of the outer assembly, the inner assembly including a second shaft, a second lumen extending through the second shaft, and a second tip removably coupled to a distal end of the second shaft, the second tip being configured to pierce tissue; and a plug assembly configured to extend through the second lumen of the inner assembly, the plug assembly including a third shaft and a plug removably coupled to a distal end of the third shaft.

The first tip may include a first tip lumen, the second tip may extend through the first tip lumen, and the second tip may include a protrusion configured to engage with the first tip and secure the first tip to the second tip. The protrusion may extend proximally from a proximal end of the second tip, and is configured to engage with a proximal end of the first tip via a snap-fit. The first tip may include a first bevel at a distal end of the first tip. The second tip may include a second bevel configured to pierce tissue at a distal end of the second tip. The second tip may include a first flange extending proximally from the second bevel at an angle offset from a longitudinal axis of the second tip. The first flange may include a first part and a second part pivotable relative to the first part by a hinge. In a first configuration, the second part may extend at a first angle to the longitudinal axis of the second tip, and in a second configuration, the second part may extend at a second angle to the longitudinal axis of the second tip, wherein the second angle is different than the first angle. Pulling the inner assembly proximally may cause the second part to pivot from the first configuration to the second configuration. The hinge may be a living hinge. The second tip may include a second tip lumen extending through the second tip, an inner surface surrounding a distal portion of the second tip lumen, and a second flange extending radially inward from the inner surface and surrounding a proximal portion of the second tip lumen. The plug may be a solid member without lumens, may include a bevel at a distal end, and may include a third flange extending circumferentially around a portion of the plug, wherein a distally-facing surface of the third flange is configured to abut a proximal-facing surface of the second flange when the plug is extended through the second lumen. The second tip may include a recess at a distal end of the second tip, the recess extending only partially around a circumference of the second tip, and the plug may include a protrusion configured to be received by the recess, the protrusion extending only partially around a circumference of the plug. One or more of the first tip, the second tip, and the plug may be bioresorbable. Each of the first tip, the second tip, and the plug may be bioresorbable.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 19-24 illustrate a plug assembly having a plug according to an example of the present disclosure.

FIGS. 34-36 illustrate another embodiment of a piercing tip for use with an inner assembly.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or like parts or components. The term "distal" refers to the direction that is away from the user or operator and into the patient's body.

By contrast, the term "proximal" refers to the direction that is closer to the user or operator and away from the patient's body.

The present disclosure is directed to devices for accessing a blood vessel, such as, e.g., a femoral artery, a carotid artery, or any other artery or vein. An exemplary method is shown in FIGS. 1-3, 3A, and 4-6 using a medical kit. The medical kit is described in more detail with reference to FIGS. 7-30.

Figure 7:
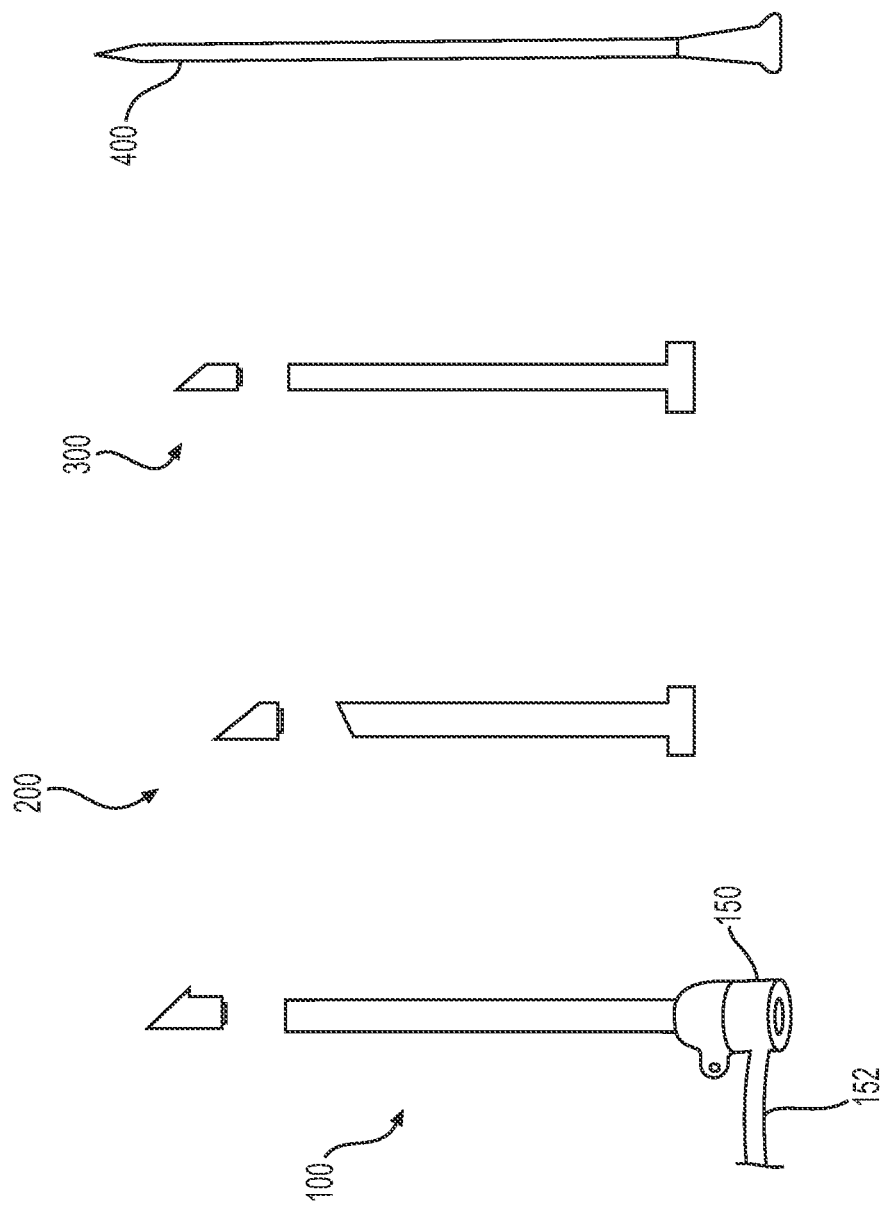
FIG. 7 illustrates various components of a medical kit according to an example of the present disclosure.
Figure 8:
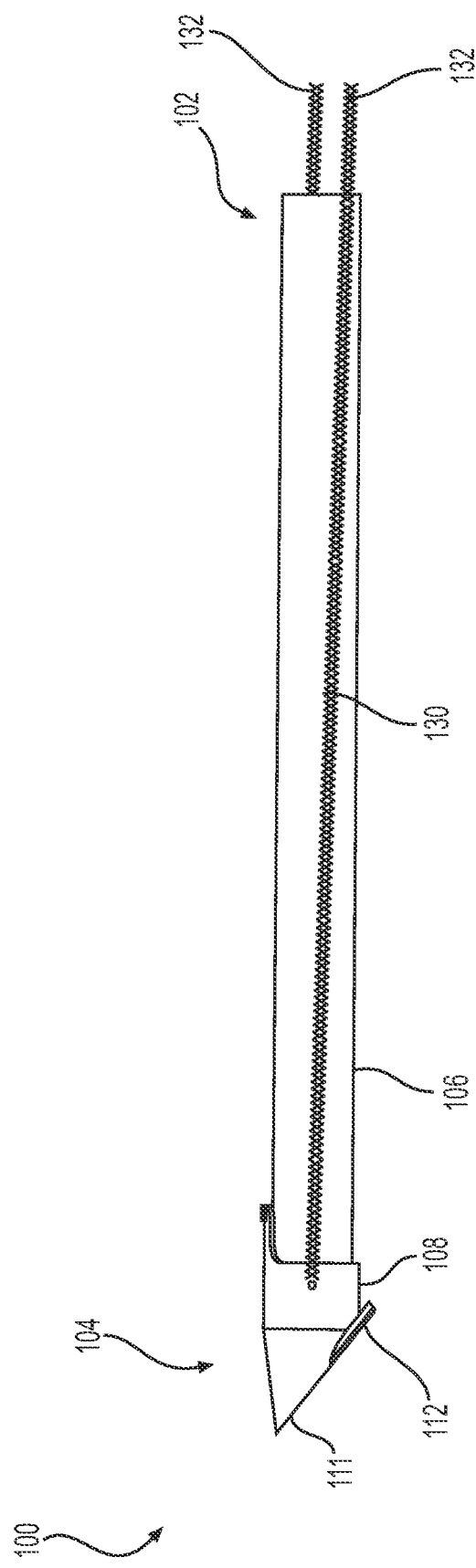
FIGS. 8-12 illustrate an inner assembly having a piercing tip according to an example of the present disclosure.
Figure 9:
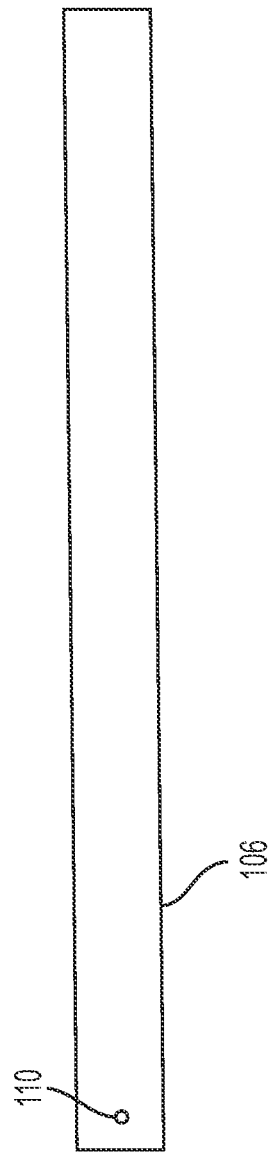
Figure 12:
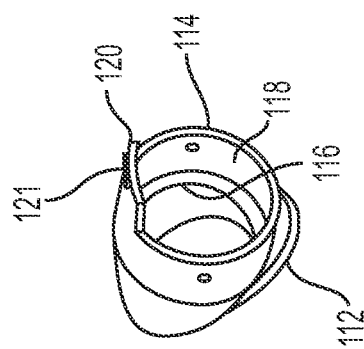
Figure 11:
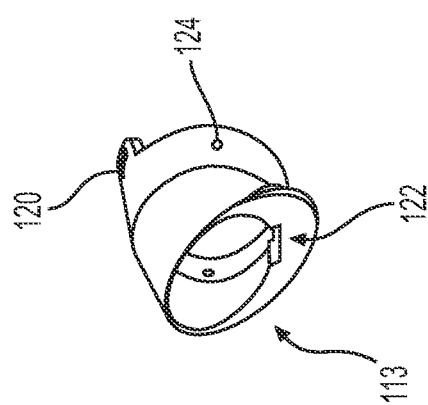
Figure 10:
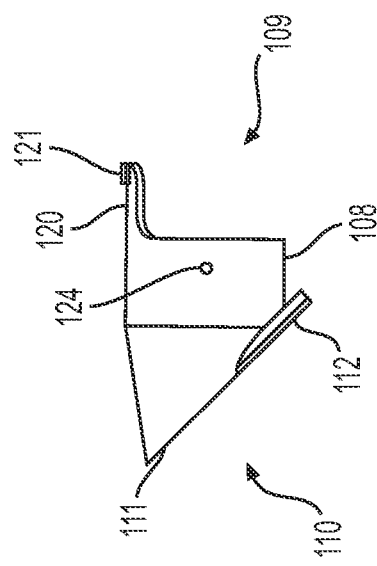
Figure 13:
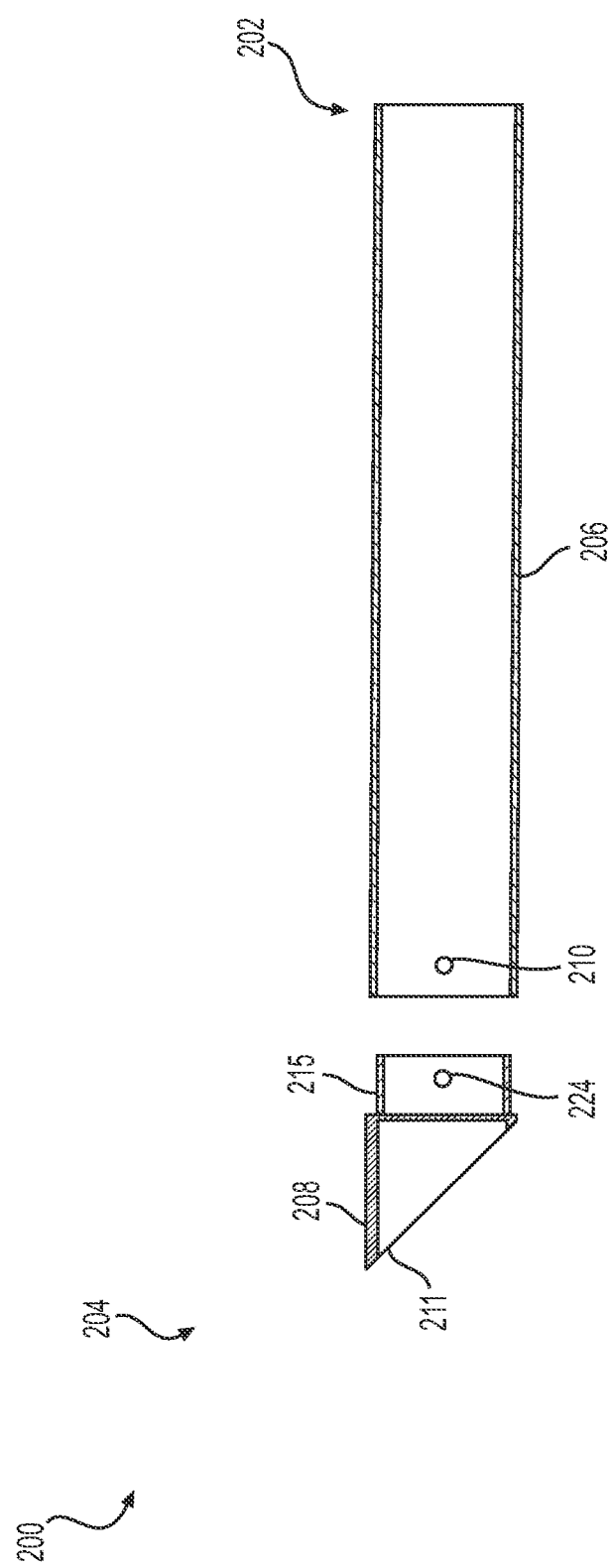
FIGS. 13-18 illustrate an outer assembly having a distal tip according to an example of the present disclosure.
Figure 14:
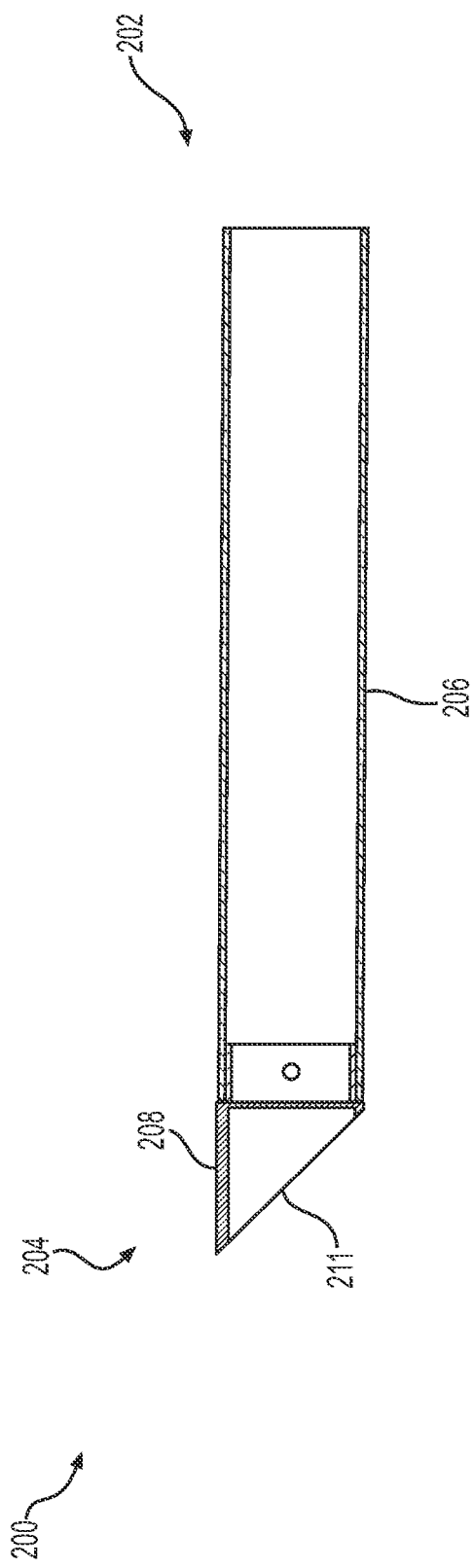
Figure 15:
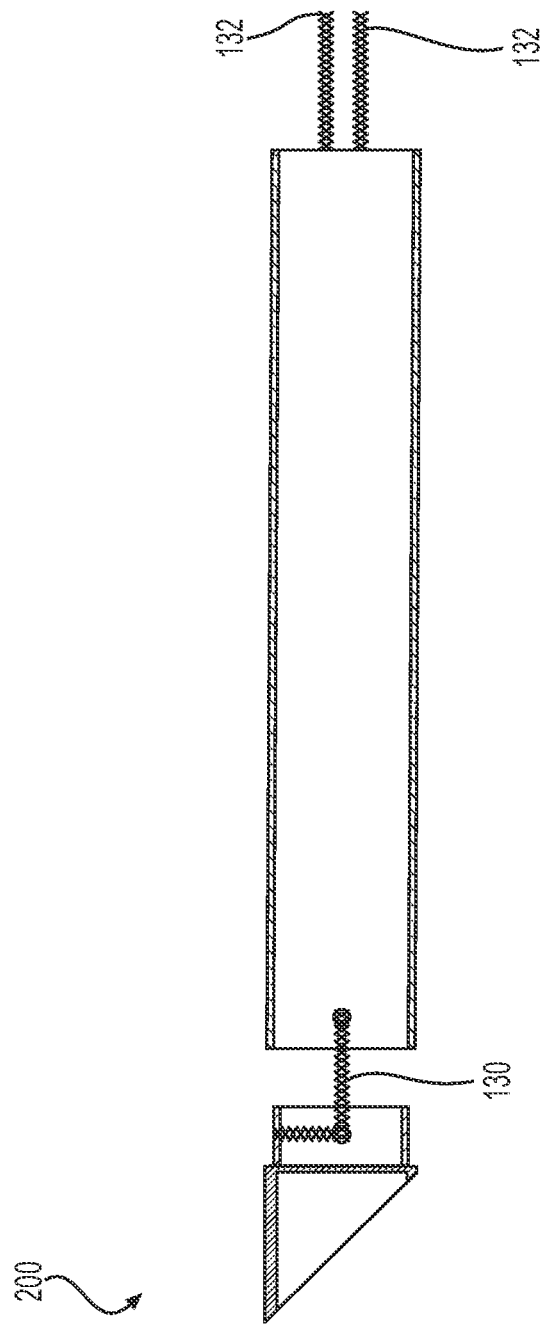
Figures 16, 17, 18:
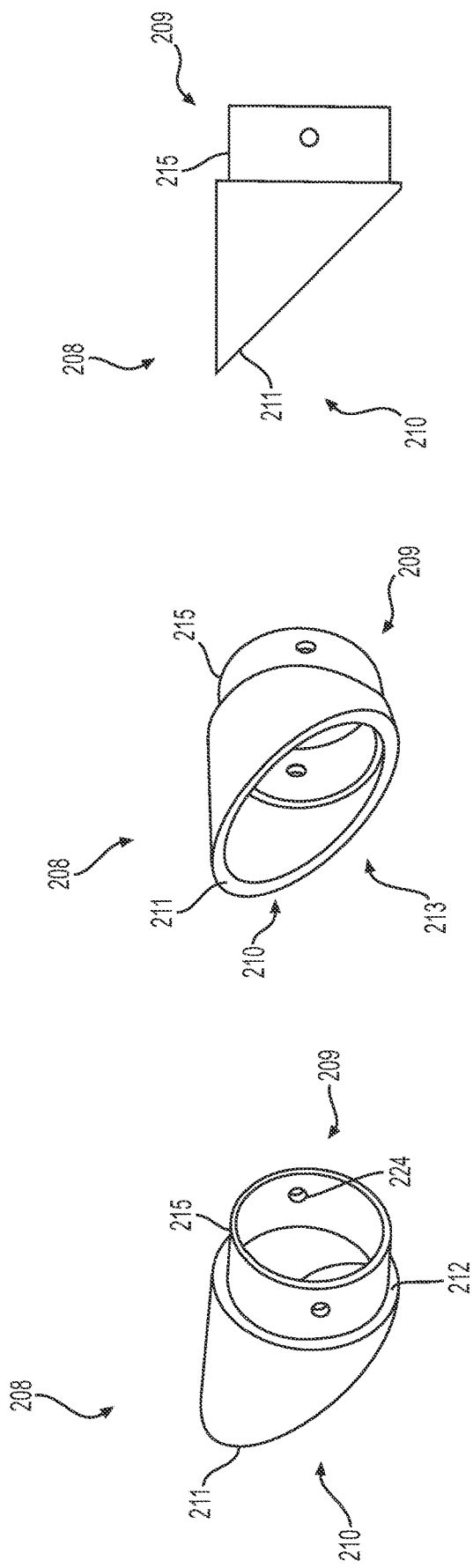
Figure 19:
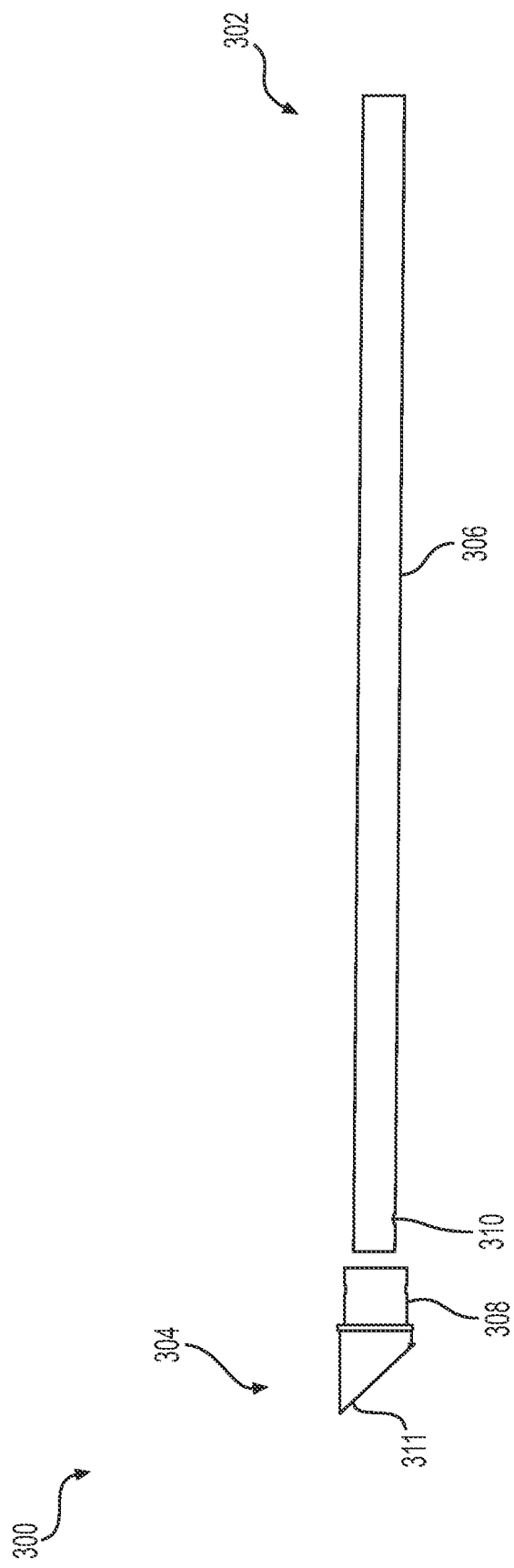
Figure 20:
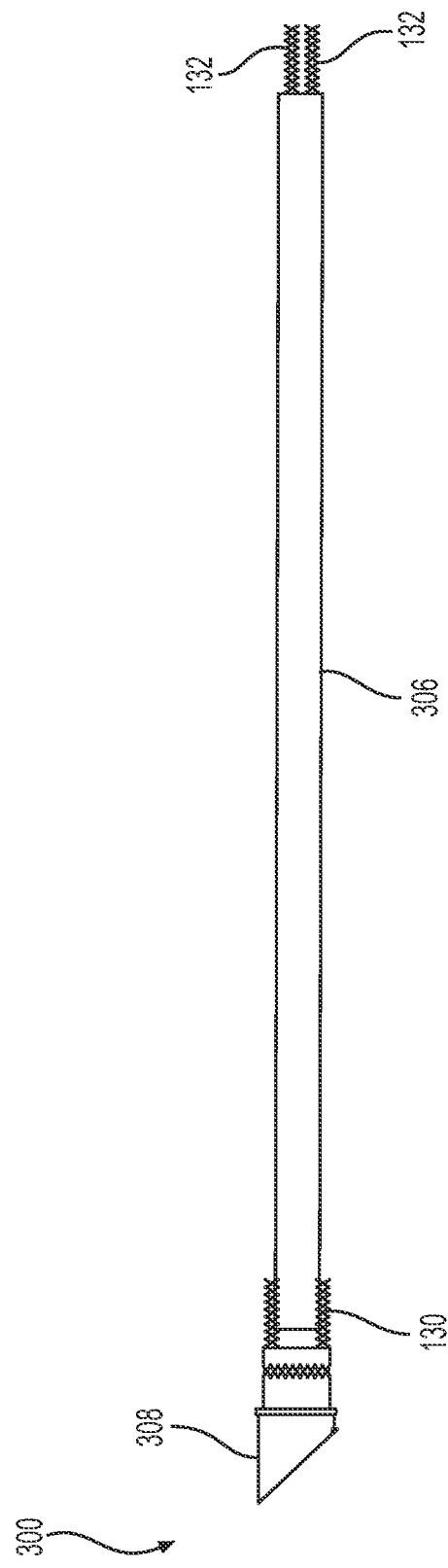

Referring to FIG. 7, the medical kit may include an inner assembly 100, an outer assembly 200, a plug assembly 300, and a dilator 400. Dilator 400 may be any suitable device configured to dilate a body lumen, including expandable dilators. Dilator 400 may be removably coupled to inner assembly 100 so that dilator 400 and inner assembly 100 may be inserted simultaneously into a blood vessel.

Various portions of inner assembly 100 are shown in FIGS. 8-12. Inner assembly 100 may extend from a proximal end 102 to a distal end 104, and may include a shaft 106 that is coupled to a piercing tip 108 at distal end 104. The shaft 106 may include one or more lumens extending therethrough. Shaft 106 also may include one or more openings 110 extending through a wall of shaft 106. In one example, shaft 106 may include two diametrically opposed openings 110 near its distal end.

Piercing tip 108 has a body that extends from a proximal end 109 to a distal end 110, and may include a bevel 111 at distal end 110 that is configured to pierce through tissue. Piercing tip 108 also may include a flange 112 that extends proximally from bevel 111. In some examples, flange 112 may lie in the same plane as bevel 111. In some examples, flange 112 extends from only a proximal portion of bevel 111. Flange 112, and particularly its proximal-facing surface, may include a tacky coating and/or bioadhesive to help maintain flange 112 against tissue. A lumen 113 may extend from proximal end 109 to distal end 110. Piercing tip 108 may include a circumferential rim 114 at proximal end 109, and a circumferential flange 116 disposed distally of rim 114. The flange 116 may extend radially inward from an inner surface 118 of piercing tip 108. The flange 116 may have a smaller diameter than rim 114. A locking arm 120 may extend proximally from rim 114. Locking arm 120 may include a radially-outward extending protrusion 121. Piercing tip 108 also may include a recess 122 at distal end 110, which may be used in a snap fit engagement with a portion of plug assembly 300, as discussed in further detail below. Piercing tip 108 also may include one or more openings 124 extending through its body and in communication with lumen 113. In one example, piercing tip 108 may include diametrically opposed openings 124 that align with openings 110 of shaft 106.

Piercing tip 108 may be coupled to a distal end of shaft 106 via a connecting member 130. The connecting member 130 may extend outside of the one or more lumens of shaft 106 and through openings 110 of shaft 106 and openings 124 of piercing tip 108, to secure the piercing tip 108 to shaft 106. The connecting member 130 may be a suture, wire, thread, or other suitable connecting member. Opposing ends 132 of connecting member 130 may extend proximally when piercing tip 108 and shaft 106 are coupled to one another. In one example, tension may be applied to those ends 132. Piercing tip 108 may be configured to detach from shaft 106. In one example, tension may be released from one of the ends 132, allowing connecting member 130 to be removed from the device by pulling on the other end 132. In another example, connecting member 130 may include one or more frangible links that are configured to break when a sufficient pulling force is applied to ends 132, allowing separation of piercing tip 108 from shaft 106.

Referring to FIG. 7, inner assembly 100 may include an access port 150 and a conduit 152 at proximal end 102. Access port 150 may be used to deliver various tools through one or more lumens of inner assembly 100, and conduit 152 may be used for suction, irrigation, aspiration, or other fluid-related tasks. In one example, conduit 152 may be used to provide a saline flush. A pressure sensor may disposed in access port 150 or in another suitable location of inner assembly 100 to monitor pressure within a blood vessel.

Various portions of outer assembly 200 are shown in FIGS. 13-18. Outer assembly 200 may extend from a proximal end 202 to a distal end 204, and may include a shaft 206 that is coupled to a distal tip 208 at distal end 204. The shaft 206 may include one or more lumens extending therethrough. Shaft 206 also may include one or more openings 210 extending through a wall of shaft 206. In one example, shaft 206 may include two diametrically opposed openings 210 near its distal end.

Distal tip 208 has a body that extends from a proximal end 209 to a distal end 210, and may include a bevel 211 at distal end 210 that is configured to clamp onto tissue. In some examples, the bevel 211 may be atraumatic to prevent excessive damage to tissue when used as a clamp. Bevel 211 may include a tacky coating and/or bioadhesive in order to help secure bevel 211 against tissue. A gauze or other fabric may be coupled to bevel 211 to absorb excess bodily fluids and to facilitate healing during closure of an access opening to a blood vessel. Proximal end 209 may include a generally cylindrical portion 215 configured to slide into a lumen of shaft 206. Distal tip 208 also may include a proximally-facing circumferential flange 212 configured to abut the distal end of shaft 206. A lumen 213 may extend from proximal end 209 to distal end 210. Distal tip 208 also may include one or more openings 224 extending through cylindrical portion 215 and in communication with lumen 213. In one example, distal tip 208 may include diametrically opposed openings 224 that align with openings 210 of shaft 206.

Distal tip 208 may be coupled to a distal end of shaft 206 via a connecting member 130 that is substantially similar to the connecting member 130 previously described. The connecting member 130 may extend through openings 224 of distal tip 208 and at least partially around a circumference of cylindrical portion 215. The ends 132 of the connecting member 130 then may be passed through openings 210 of shaft 206, the lumen of shaft 206, and proximally out of shaft 206.

Various portions of plug assembly 300 are shown in FIGS. 19-24. Plug assembly 300 may extend from a proximal end 302 to a distal end 304, and may include a shaft 306 that is coupled to a plug 308 at distal end 304. The shaft 306 may include one or more lumens extending therethrough. Shaft 306 also may include one or more openings 310 extending through a wall of shaft 306. In one example, shaft 306 may include two diametrically opposed openings 310 near its distal end.

Plug 308 has a body that extends from a proximal end 309 to a distal end 310, and may include a bevel 311 at distal end 310. In some examples, the bevel 311 may be a solid member (having no lumens or extensions therethrough) in order to seal an opening created through a wall of a blood vessel. Proximal end 309 may include a generally cylindrical portion 315 configured receive a distal end of shaft 306 in a lumen 313. Distal tip 308 also may include a circumferential flange 312 configured to abut flange 116 of inner assembly 100. Lumen 313 may extend from proximal end 309 toward distal end 310, and may be closed off at a distal end by a proximal surface of bevel 311. Plug 308 also may include one or more openings 324 extending through cylindrical portion 315 and in communication with lumen 313. In one example, plug 308 may include diametrically opposed openings 324 that align with openings 310 of shaft 306. Plug 308 also may include a locking protrusion 330 extending radially outward from a proximalmost portion of the bevel 311. As shown in FIG. 22, plug 308 may be covered with a graft 340, such as, e.g., an ePTFE graft to promote tissue growth after insertion through a blood vessel wall.

Distal tip 308 may be coupled to a distal end of shaft 306 via a connecting member 130 that is substantially similar to the connecting member 130 previously described. The connecting member 130 may extend through openings 324 of plug 308 and at least partially around a circumference of cylindrical portion 315. The ends 132 of the connecting member 130 then may be passed through openings 310 of shaft 306, a lumen of shaft 306, and proximally out of shaft 306.

All or portions of inner assembly 100, outer assembly 200, and plug assembly 300 may be formed from biocompatible materials. Examples of such materials may include, but are not limited to, polytetrafluoroethylene (PTFE), expanded polytetrafluoroethylene (ePTFE), ethylene tetrafluoroethylene (ETFE), polyethylene terephthalate (PET), perfluoroalkoxy (PFA), polyether ether ketone (PEEK), polypropylene (PP), silicone, polycarbonate, polyurethane, LDPE, HDPE or the like. In some embodiments, one or more portions of the inner assembly 100, outer assembly 200, and plug assembly 300, may be formed from bioresorbable materials, including, for example, polyglycolide (PGA), polylactide (PLA), and/or polycaprolactone (PCL). When bioresorbable materials are used, different bioresorbable materials may be used that regrade at different rates. In one example, one or more of piercing tip 108, distal tip 208, and plug 308 may include a bioresorbable material.

Figure 25:
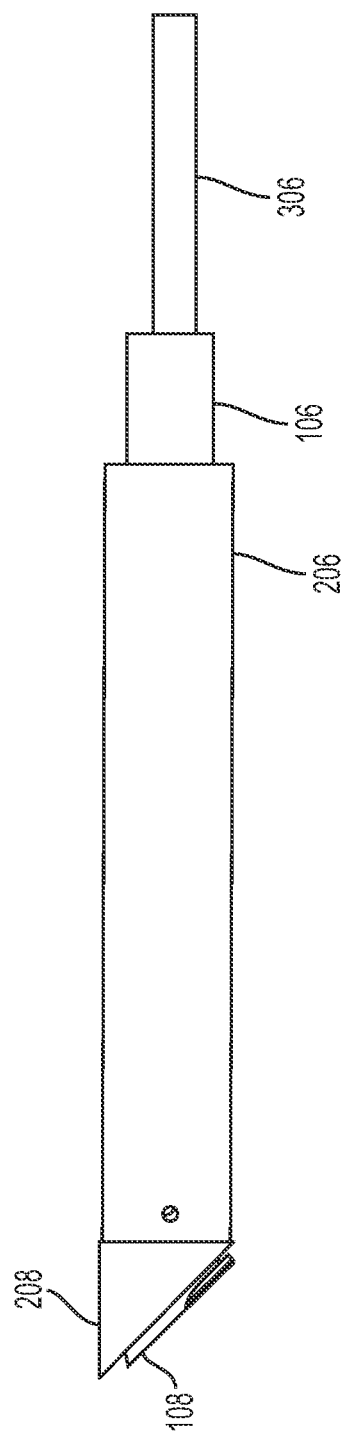
FIGS. 25-30 illustrate the inner assembly of FIGS. 8-12, the outer assembly of FIGS. 13-18, and the plug assembly of FIGS. 19-24 used together in various configurations.
Figure 26:
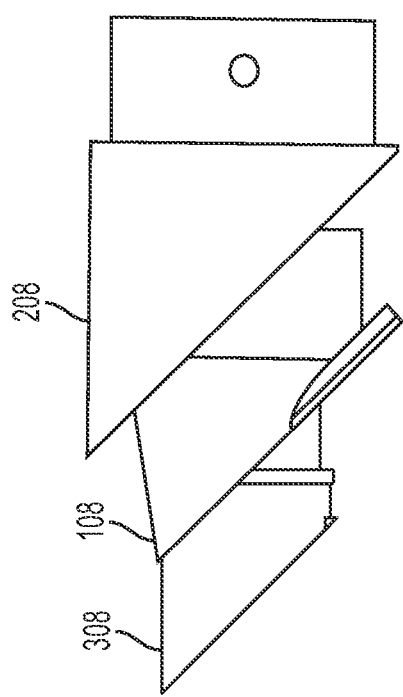
Figure 27:
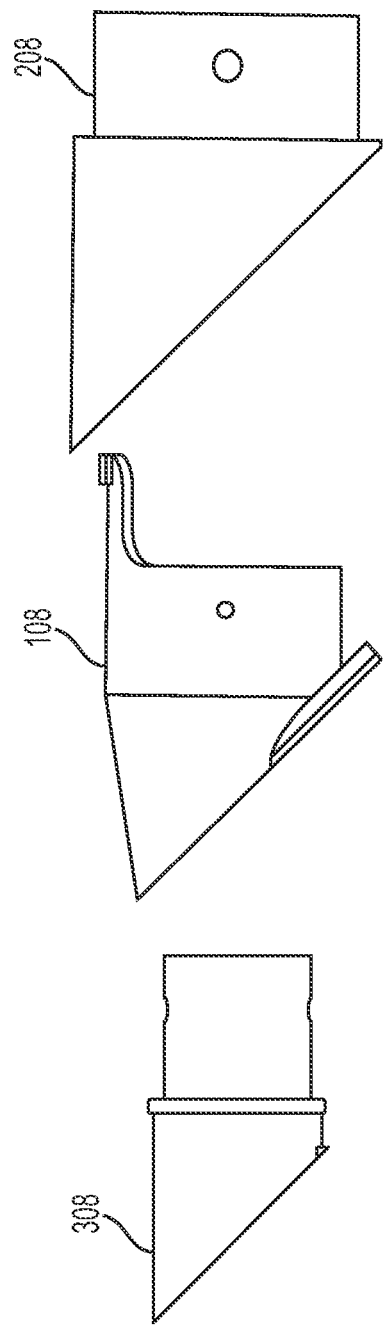
Figure 30:
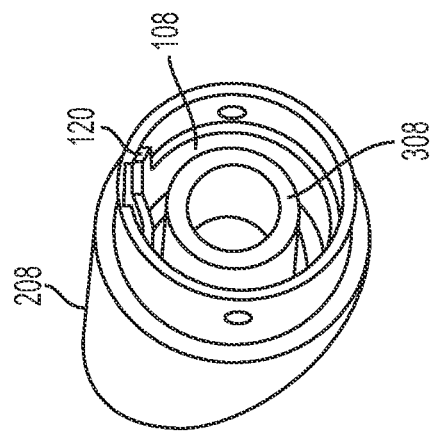
Figure 28:
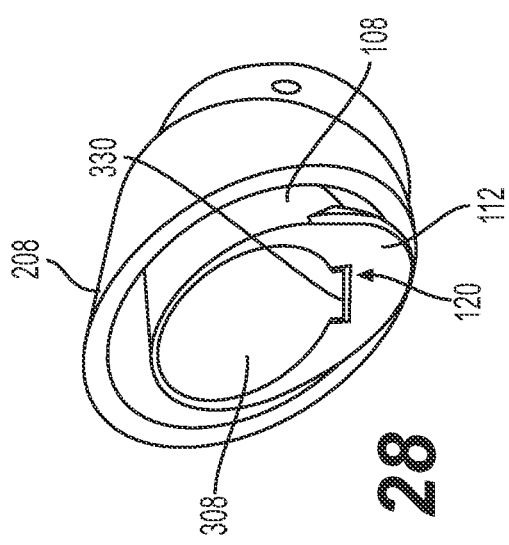
Figure 29:
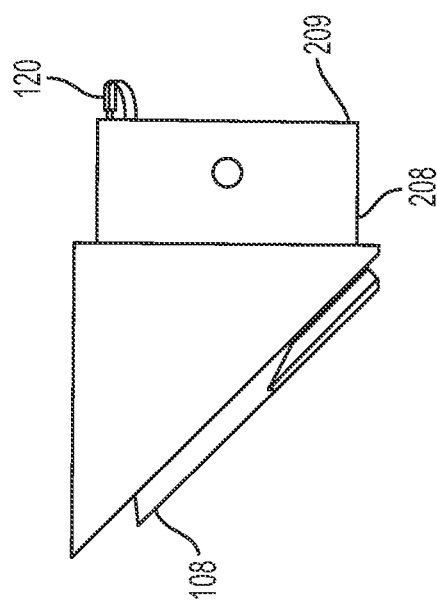

FIGS. 25-30 show the relationship of inner assembly 100, outer assembly 200, and plug assembly 300. In one example, outer assembly 200 may be configured to surround inner assembly 100, and thus, inner assembly 100 may have a smaller diameter than outer assembly 200 so as to fit within a lumen of outer assembly 200. Further, plug assembly 300 may be configured to slide within a lumen of inner assembly 100 as shown in FIG. 25. Thus, shafts 206, 106, and 306 may be nested in certain configurations of the medical kit. Additionally, distal tip 208, piercing tip 108, and plug 308 may be nested in certain configurations, with distal tip 208 surrounding piercing tip 108, and piercing tip 108 surrounding plug 308.

Distal tip 208 and piercing tip 108 may have corresponding features that cooperate to secure distal tip 208 and piercing tip 108 together. For example, locking arm 120 of inner assembly 100 may be configured to engage proximal end 209 of distal tip 208. For example, distal tip 208 may be advanced distally over piercing tip 108 until locking arm 120 clears proximal end 209 of distal tip 208, causing distal tip 208 and piercing tip 108 to form a locked configuration relative to one another. The protrusion 121 of locking arm 120 may engage proximal end 209 of distal tip 208. Also, locking arm 120 may be a cantilevered arm that may flex radially inward and outward during engagement with distal tip 208. Once locking arm 120 clears proximal end 209, piercing tip 108 may be prevented from moving distally relative to distal tip 208 due to the engagement of locking arm 120 with proximal end 209 of distal tip 208.

Piercing tip 108 and plug 308 also may have corresponding features that cooperate to secure piercing tip 108 to plug 308. For example, piercing tip 108 includes a recess 122 configured to receive locking protrusion 330 of plug 308. Also, flange 116 of piercing tip 108 may be configured to abut the distally-facing surface of flange 312. Thus, in some examples, plug 308 may be advanced distally through the proximal end 109 of piercing tip 108 until locking protrusion 330 engages with recess 122. Once locking protrusion 330 engages with recess 122, plug 308 may be prevented from moving proximally relative to piercing tip 108 due to the engagement of locking protrusion 330 and recess 122. In some examples, the engagement of locking protrusion 330 with recess 122 may require precise circumferential alignment between piercing tip 108 and plug 308. Additionally, plug 308 may be prevented from moving distally relative to piercing tip 108 due to the engagement of flange 116 and flange 312.

Figure 1:
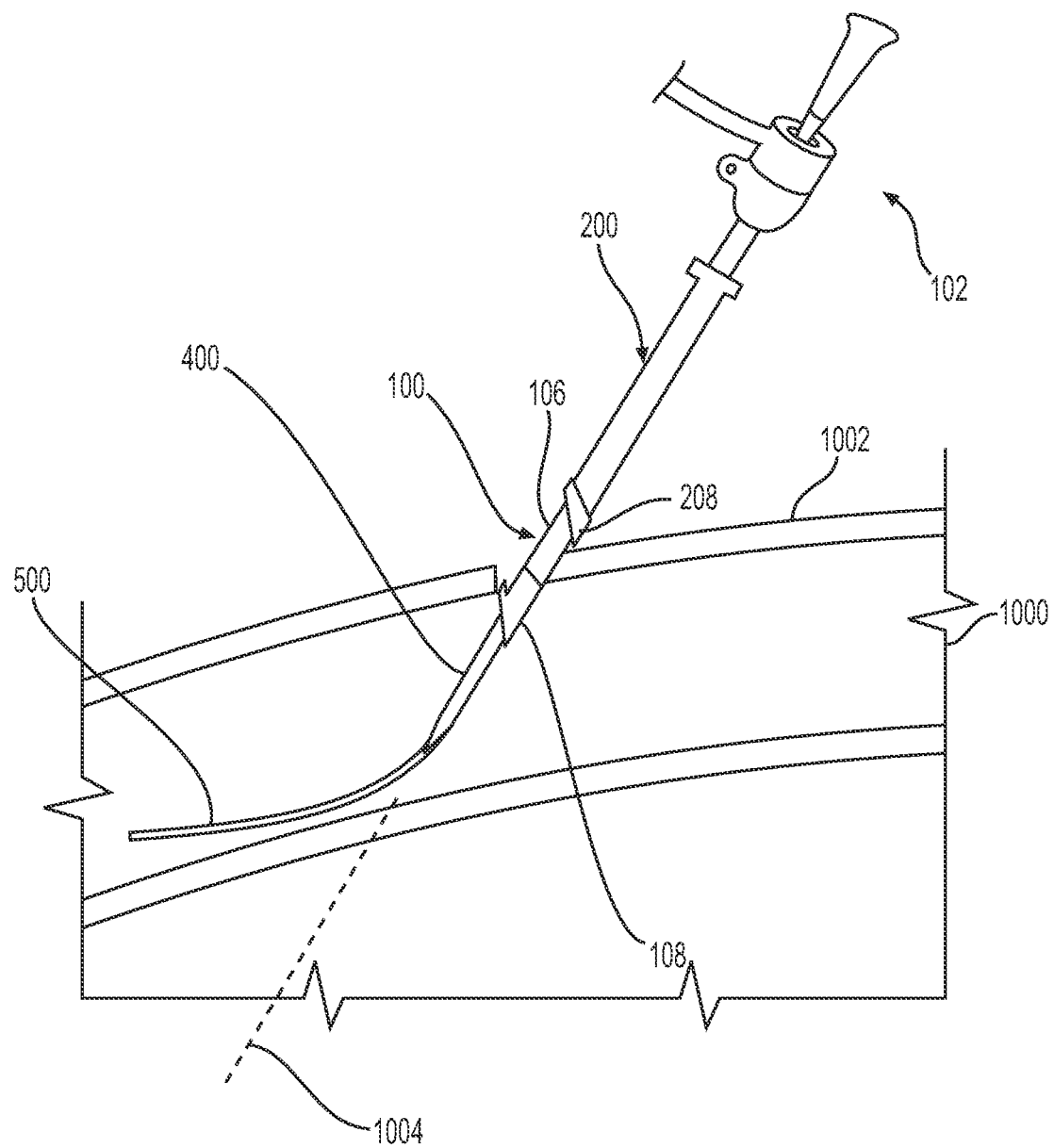
FIGS. 1-3, 3A, and 4-6 illustrate a method of accessing a blood vessel for a procedure, and for sealing the blood vessel after the procedure.

FIGS. 1-6 illustrate a method of accessing a blood vessel 1000 using the medical kit described with reference to FIGS. 7-30. Referring to FIG. 1, the method may begin with the kit in an insertion configuration where outer assembly 200 is positioned around inner assembly 100. Blood vessel 1000 may first be accessed by guidewire 500 through an opening made by any suitable puncture device (not shown), and then inner assembly 100, outer assembly 200, and dilator 400 may be advanced separately or simultaneously over guidewire 500. Once dilator 400 pierces through blood vessel wall 1002, blood may enter a side-hole of dilator 400 and travel proximally through dilator 400 so as to be visible at proximal end 102, providing a visual indication that the blood vessel 1000 has been accessed by dilator 400. Then, blood vessel 1000 may be accessed by piercing a wall 1002 with piercing tip 108 (and inner assembly 100) in a bevel up configuration where the bevel 111 faces away from the operator. Outer assembly 200 also may be in a bevel up configuration while piercing tip 108 is in the bevel up configuration. In a bevel up configuration, piercing tip 108 may initially contact tissue only with its distalmost point, whereas, in a bevel down configuration, the face of bevel 111 may make initial contact with tissue. In the bevel down configuration, the proximalmost portion of bevel 111 may contact tissue before, or at the same time, as a distalmost portion of bevel 111.

Figure 2:
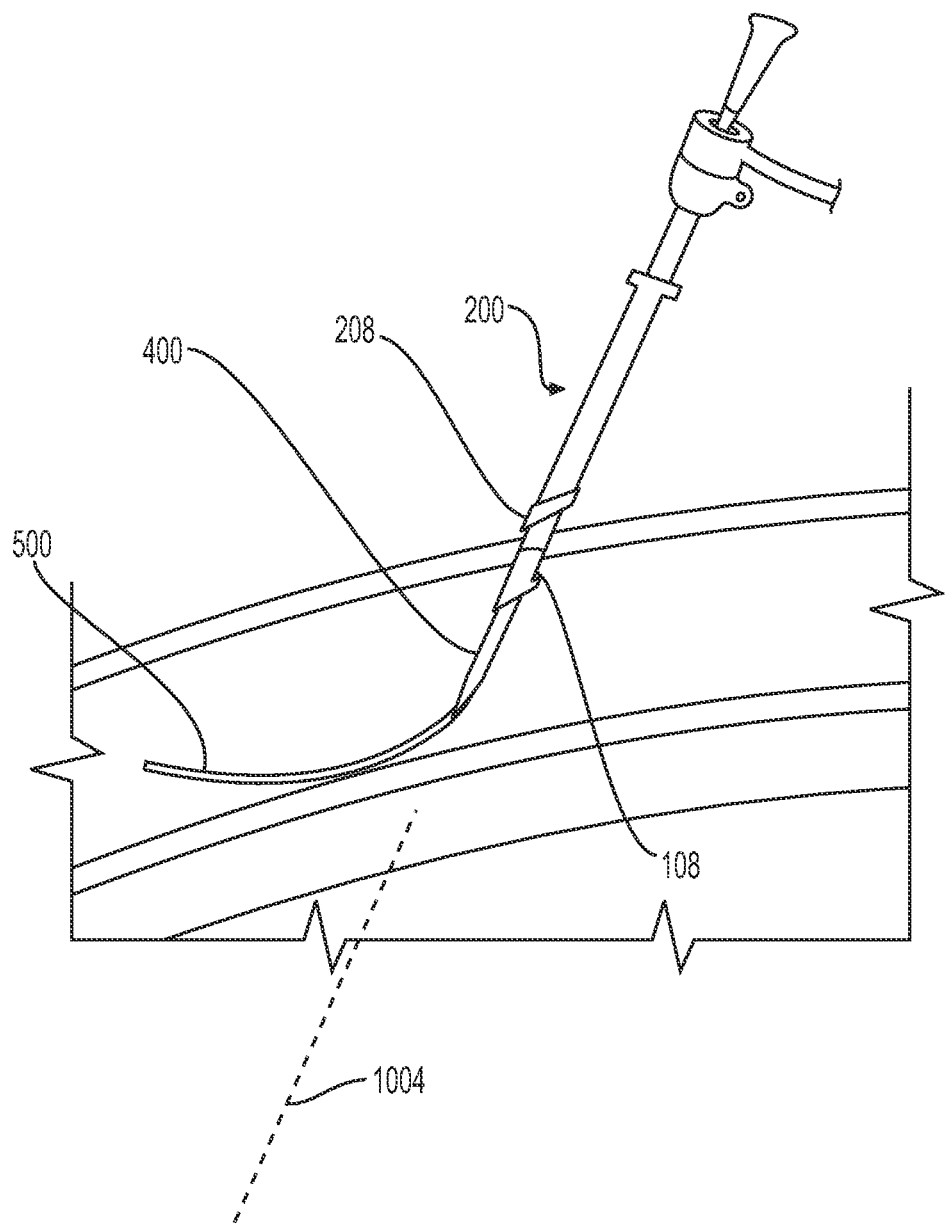

Referring to FIG. 2, an operator may rotate inner assembly 100 and/or outer assembly 200 after blood vessel 1000 has been accessed by piercing tip 108 such that both inner assembly 100 and outer assembly 200 are in a bevel down configuration where bevel 111 and 211 face toward from the user. In some embodiments, inner assembly 100 may not be rotated after blood vessel 1000 is accessed by piercing tip 108.

Figure 3:
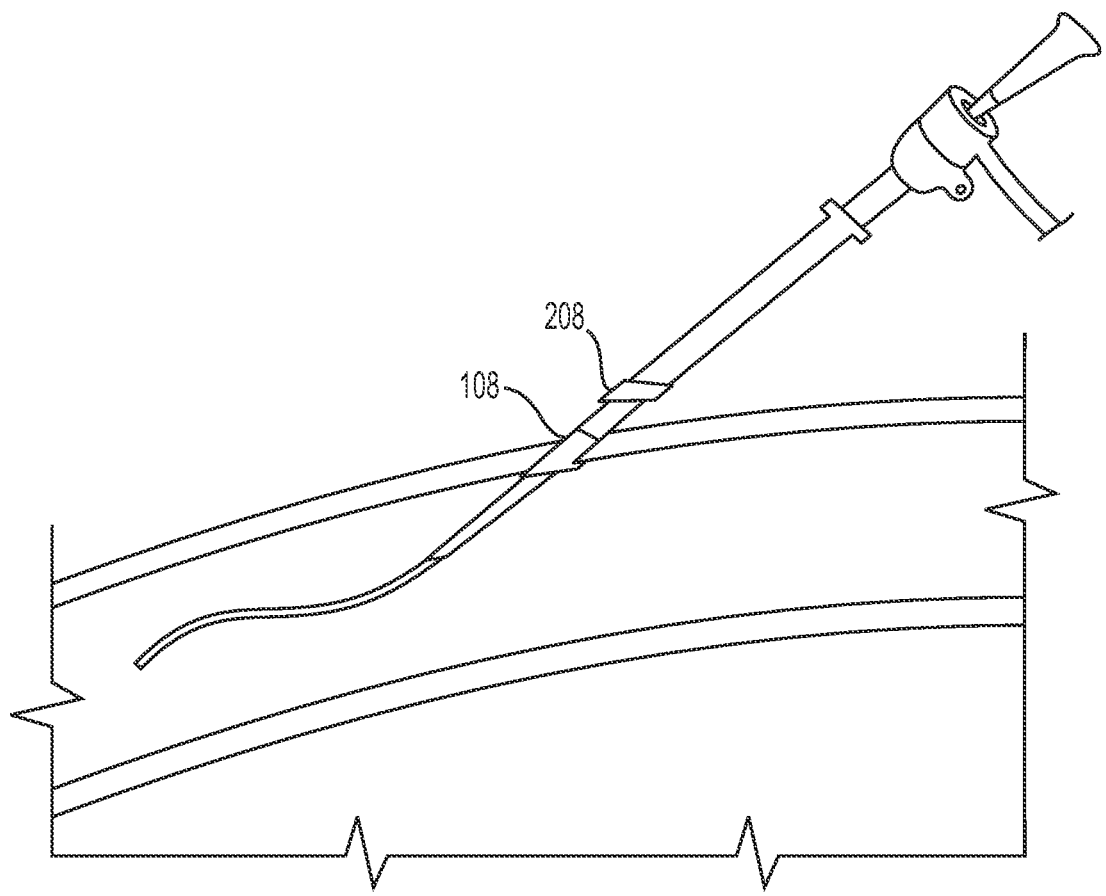
Figure 3A:
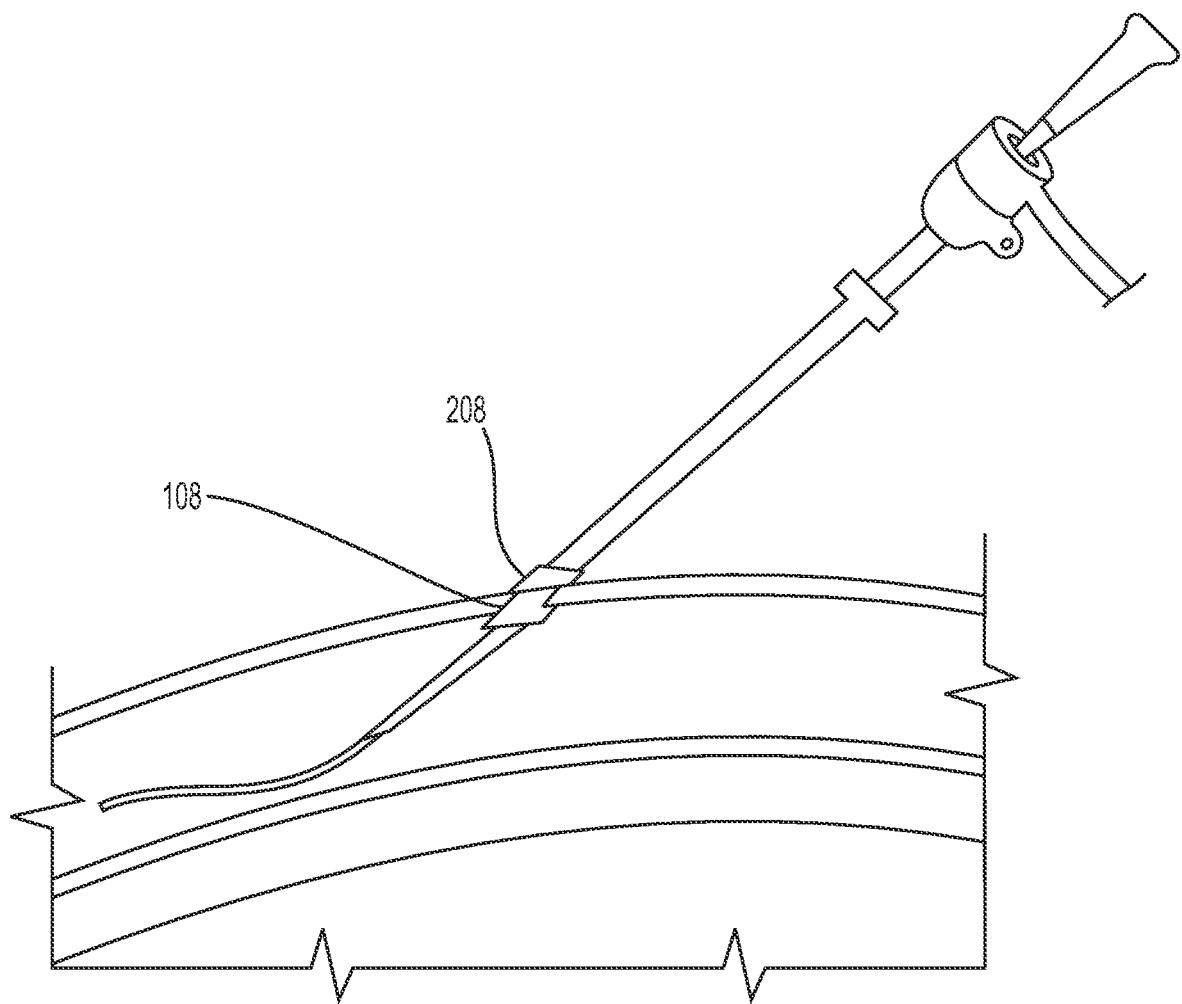
Figure 4:
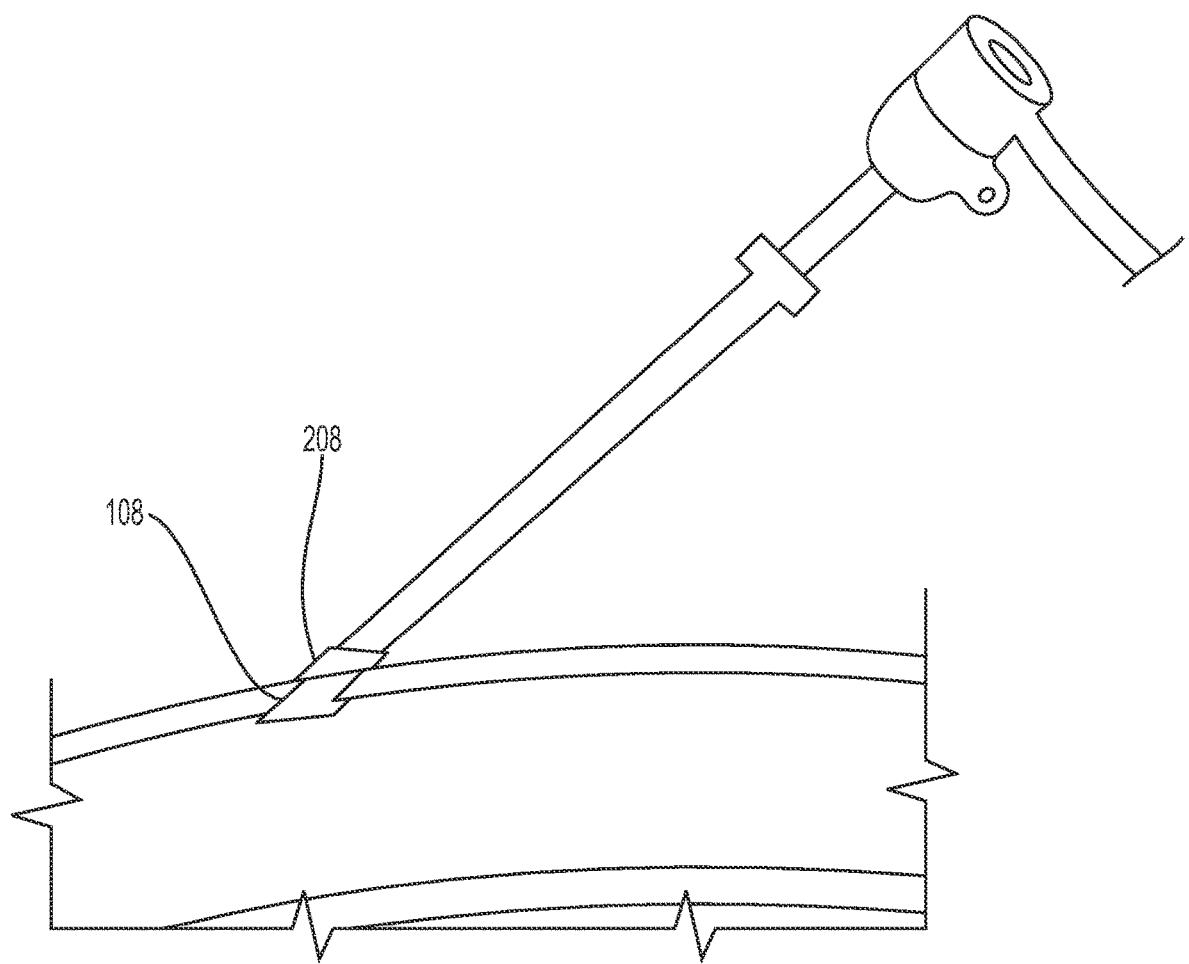
Figure 5:
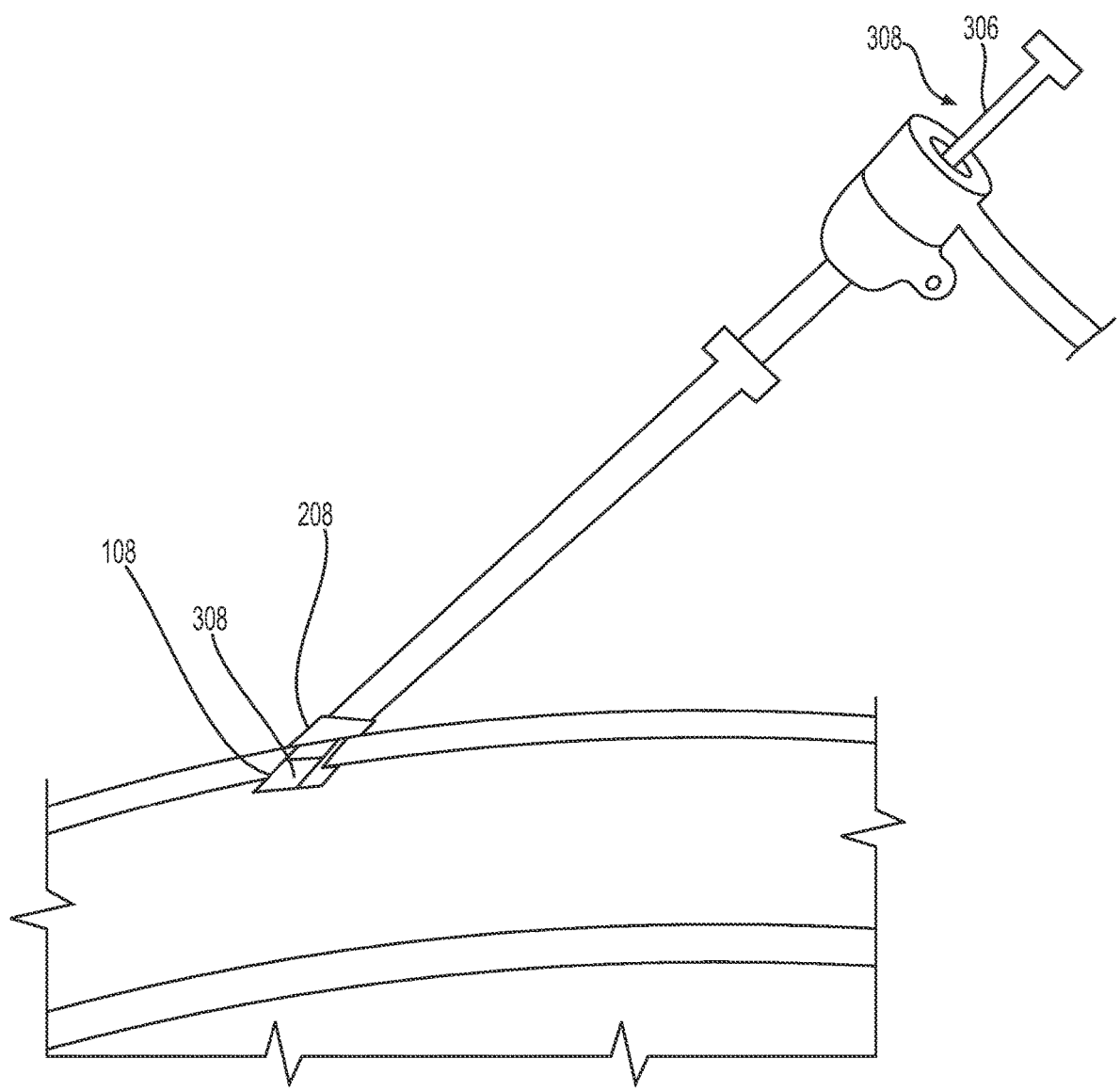
Figure 6:
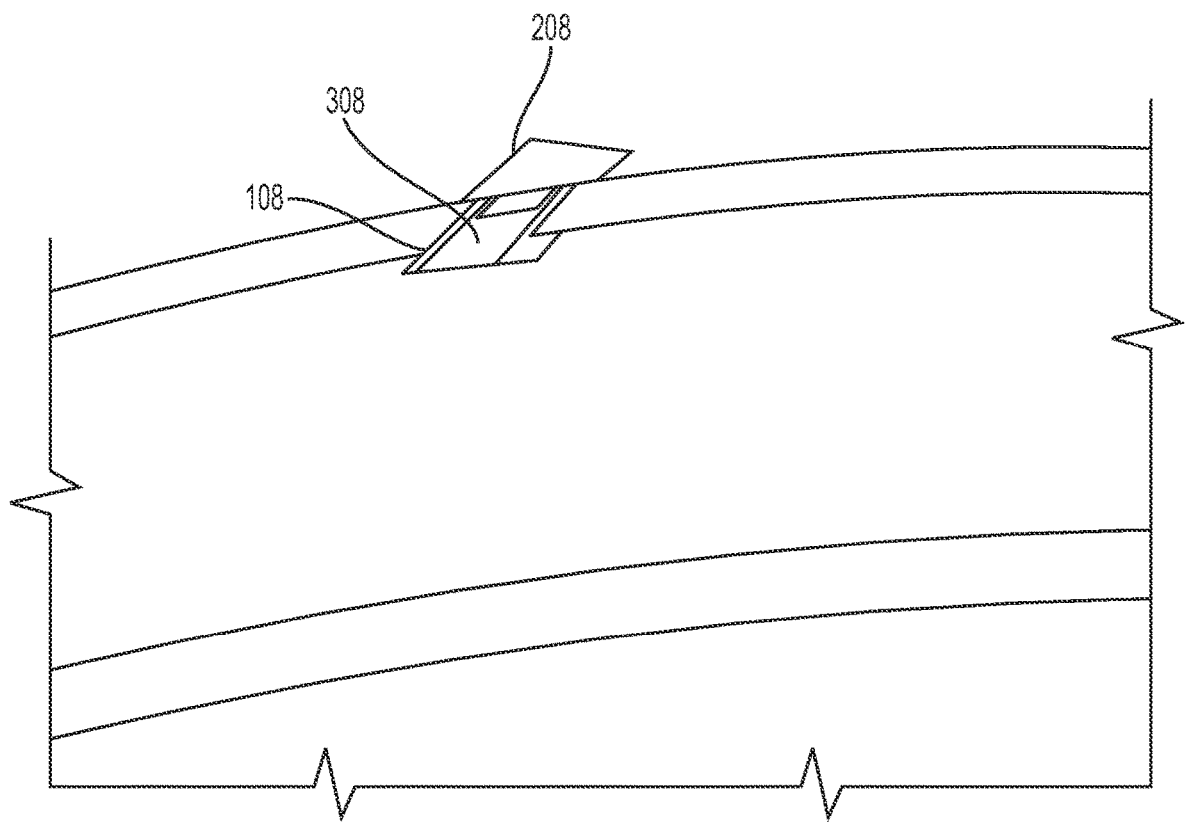

Referring to FIG. 3, once piercing tip 108 is in the bevel down configuration within blood vessel 1000, inner assembly 100 may be pulled proximally to cause flange 112 to abut the inner surface of blood vessel wall 1002. As alluded to above, inner assembly 100 may not be rotated after piercing tip 108 accesses blood vessel 1000, and inner assembly 100 may be pulled proximally while piercing tip 100 is in the bevel up configuration to cause flange 112 to abut the inner surface of blood vessel wall 1002. In some examples, the operator may be required to maintain a proximal pulling force on inner assembly 100. However, in other examples, a proximal pulling force may be maintained by various mechanical or electromechanical mechanisms so that the operator is free to perform other tasks. Referring to FIG. 3A, once flange 112 is secured against the inner surface of blood vessel wall 1002, outer assembly 200 may be pushed down (distally) such that bevel 211 (and distal tip 208 of outer assembly) comes into contact with skin or the outer surface of blood vessel wall 1002, forming a clamp with piercing tip 108. As outer assembly 200 is pushed distally, locking arm 120 (and protrusion 121) of inner assembly 100 may engage proximal end 209 of distal tip 208, securing piercing tip 108 and distal tip 208 together. Once locking arm 120 is engaged with proximal end 209 of outer assembly 200, piercing tip 108 may be prevented from moving distally relative to distal tip 208. Piercing tip 108 also may be prevented from moving further proximally due to the engagement of flange 112 with the inner surface of blood vessel wall 1002. Tacky coatings and/or bioadhesives applied to the surfaces of flange 112 and bevel 211 also may help secure piercing tip 108 and distal tip 208 in place during closure of the opening in blood vessel wall 1002.

Once piercing tip 108 and distal tip 208 are secured to one another, dilator 400 and guidewire 500 may be removed from a lumen of inner assembly 100 (FIG. 4), and a suitable therapeutic or diagnostic procedure may be performed in blood vessel 1000. The procedure may be performed in the absence of any sheath, scope, or other tool within blood vessel 1000. This may allow for easier manipulation of tools within blood vessel 1000, and for procedures to be performed both proximally and distally of the opening created in blood vessel wall 1002.

After completion of the procedure, the tools used during the procedure may be removed from blood vessel 1000, and plug assembly 300 may be inserted through inner assembly 100 (FIG. 5) until plug 308 engages with piercing tip 108 to close the opening. As set forth above, locking protrusion 330 of plug 308 may engage with recess 122 of piercing tip 108. Also, flange 116 of piercing tip 108 may be abut the distally-facing surface of flange 312 to prevent plug 308 from entering blood vessel 1000.

Once piercing tip 108, distal tip 208, and plug 308 are engaged with one another, shafts 106, 206, and 306 may be removed by pulling on connecting member ends 132 as described above. Thus, after completion of the procedure, a closure device comprising only piercing tip 108, distal tip 208, and plug 308 may remain coupled to the blood vessel wall 1002. In some examples, the entirety of the closure device may resorb within 30 to 90 days. In other examples, where the components of the closure device are non-resorbable, the closure device may be removed in a subsequent procedure, if desired.

Figure 31:
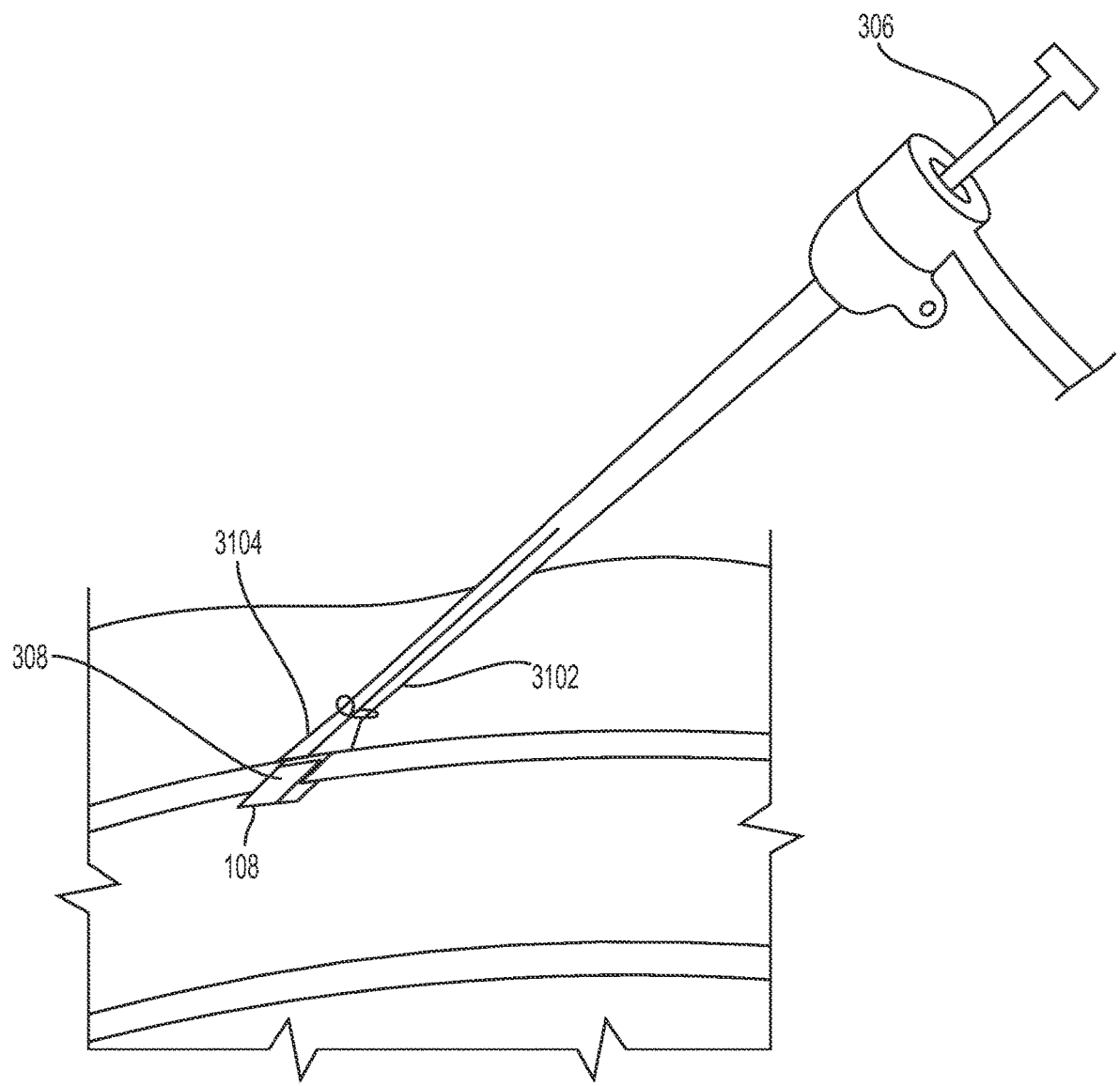
FIG. 31 is a schematic illustration of an example of closing an opening to a blood vessel using a suture.

In an alternative example shown in FIG. 31, distal tip 208 may not be used to close the opening through blood vessel wall 1002. Instead, distal tip 208 and the remainder of outer assembly 200 may be retracted proximally and/or otherwise detached from inner assembly 100 (or not used at all), and a suture knot 3102 may be used to close the opening after plug 308 has been inserted through the opening. Collagen, hydrogel, or another suitable dressing 3104 may be applied to the opening and/or suture knot 3102 to facilitate healing.

Figure 32:
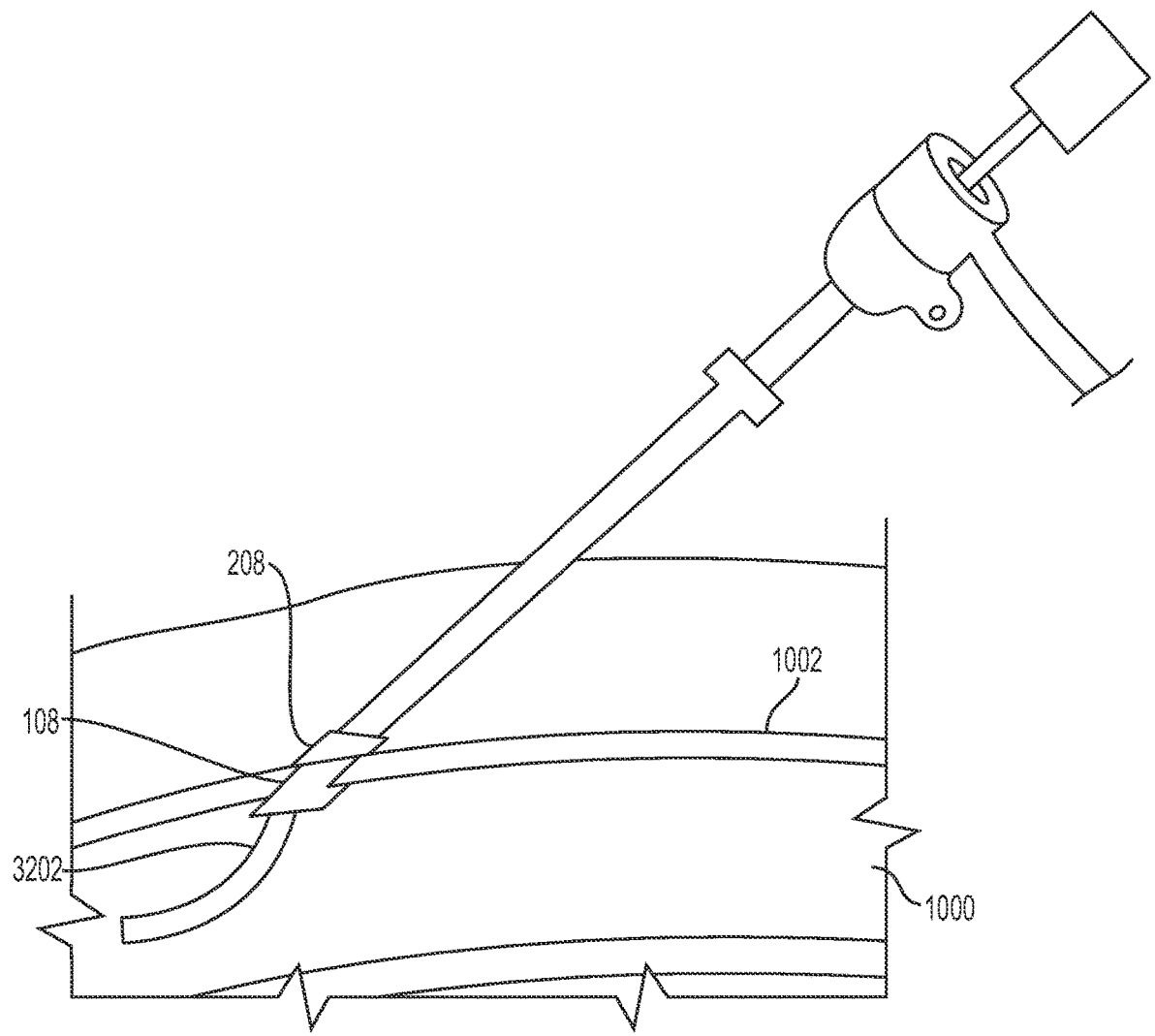
FIG. 32 is a schematic illustration of accessing a blood vessel using multiple sheaths.

In another example shown in FIG. 32, a second procedural sheath 3202 may be inserted through inner assembly 100 and into blood vessel 1000. The second procedural sheath may direct and/or divert catheters, tools, and other medical devices into the blood vessel 1000 and may help prevent puncture of an opposing surface of blood vessel wall 1002.

Figure 33:
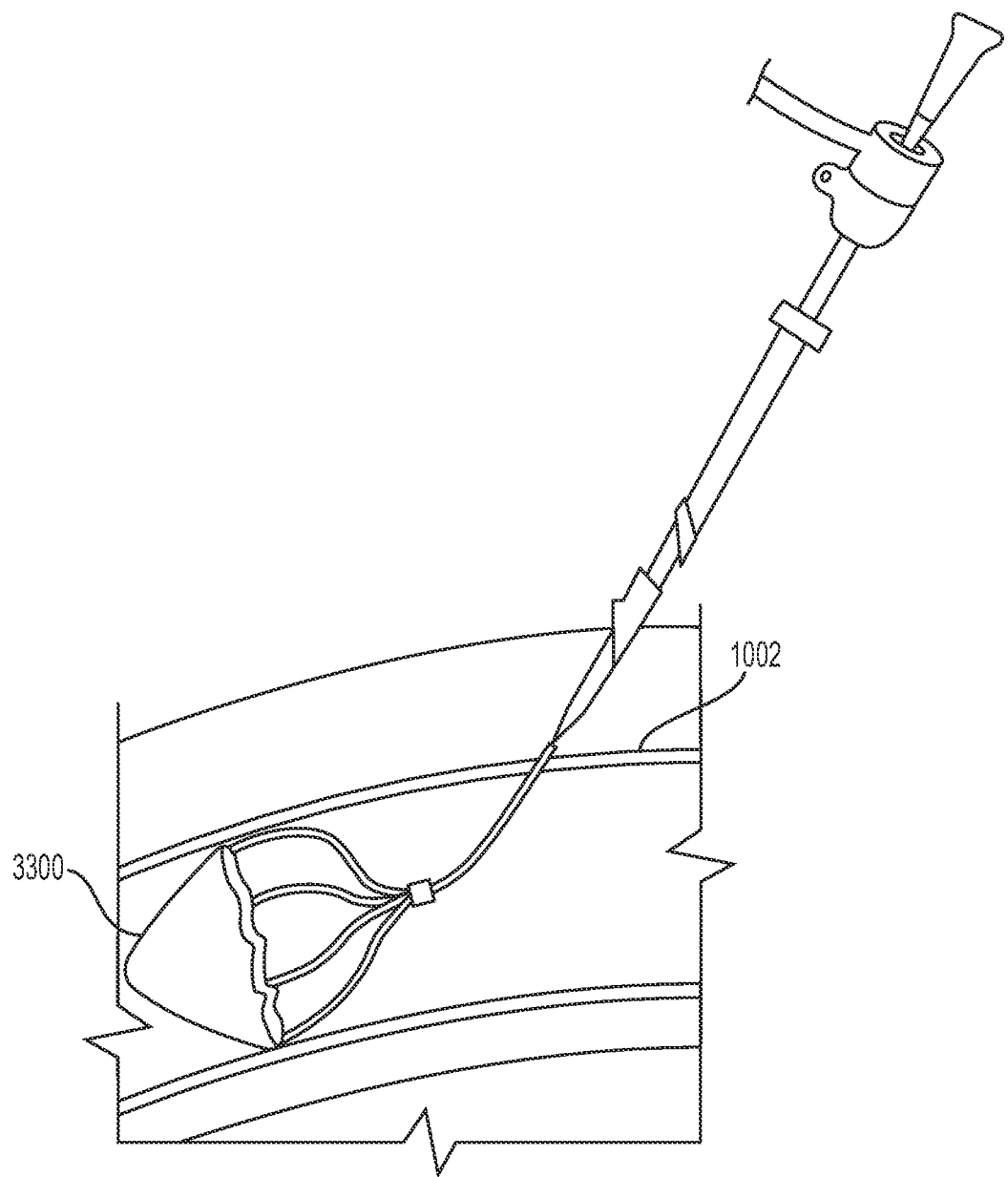
FIG. 33 is a schematic illustration of a filter assembly in a blood vessel.

In yet another example shown in FIG. 33, a filter system 3300 may be placed into blood vessel 1000 downstream of the opening through blood vessel wall 1002. Placement of the filter system 3300 downstream of the opening may help capture tissue or other materials that come loose and enter the bloodstream, helping to prevent an embolism caused by the loose materials. In one example, the filter system 3300 is used when blood vessel 1000 is the carotid artery.

Figure 35:
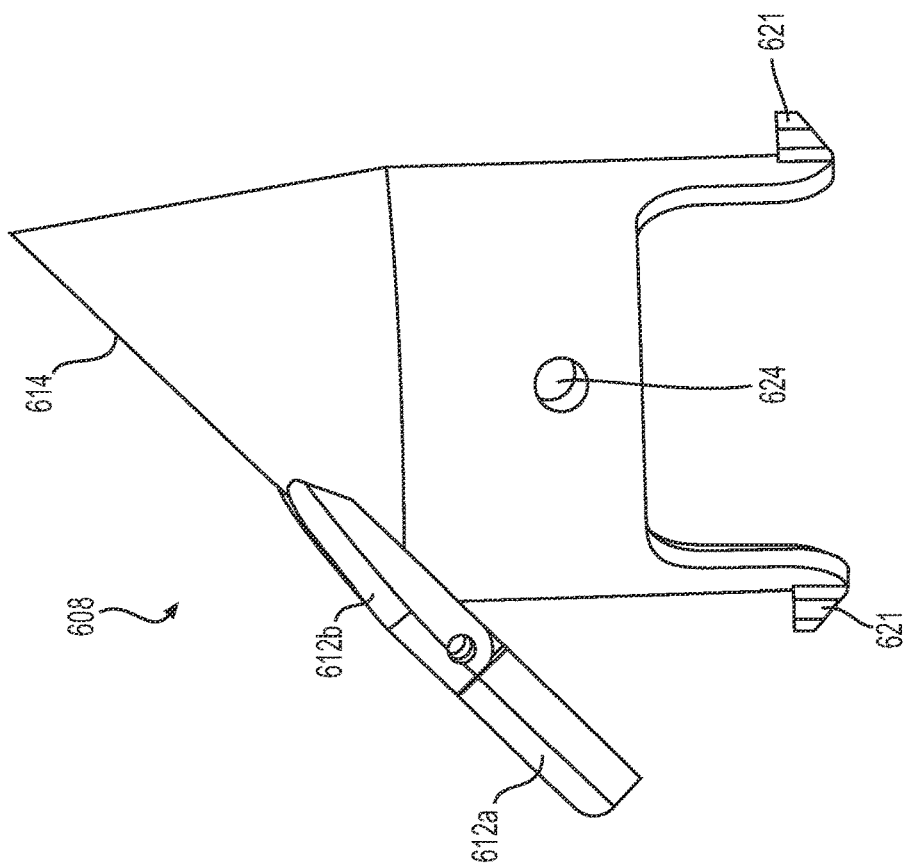
Figure 34:
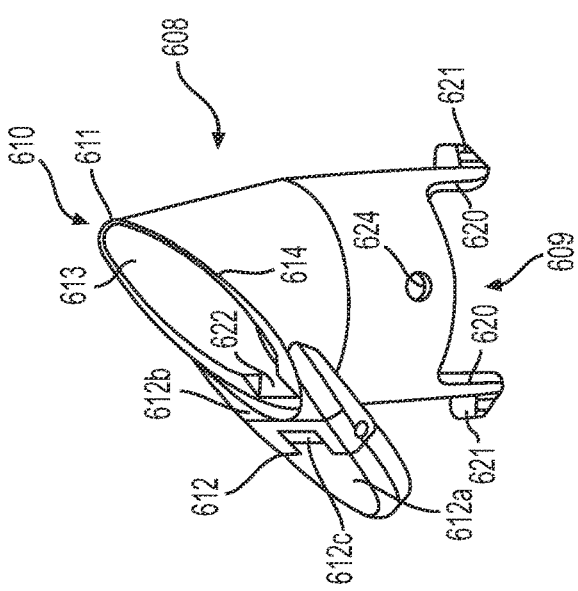

FIGS. 34-36 illustrate another embodiment of a piercing tip for use with an inner assembly in the same way that other piercing tips are used with an inner assembly throughout this disclosure. Piercing tip 608 has a body that extends from a proximal end 609 to a distal end 610, and may include a bevel 611 at distal end 610 that is configured to pierce through tissue. Piercing tip 608 also may include a flange 612 that extends proximally from bevel 611. Flange 612 will be described in more detail below. A lumen 613 may extend from proximal end 609 to distal end 610. Piercing tip 608 may include a circumferential rim 614 at proximal end 609, and a circumferential flange (not shown) disposed distally of rim 614, as in embodiments described above. The circumferential flange may have the characteristics and structure of the like-flange described in connection with those other embodiments. Two locking arms 620 extend proximally from rim 614, 180 degrees apart from each other. Each locking arm 620 includes a radially-outward extending protrusion 621. Piercing tip 108 also may include a recess 622 at distal end 610, which may be used in a snap fit engagement with a portion of plug assembly 300, as discussed in further detail above. Piercing tip 608 also may include one or more openings 624 extending through its body and in communication with lumen 613, for the same purposes as like-openings described in connection with other embodiments within this disclosure. In an example, piercing tip 608 may include diametrically opposed openings 624 that align with openings 110 of shaft 106.

As shown in FIGS. 34-36, flange 612 includes two parts 612a and 612b coupled together by a pivot/hinge 612c. Parts 612a, 612b and hinge 612c may be constructed as a one-piece, integral structure (for example, molded) or as multiple pieces coupled together by, for example, a pivot pin. If a one piece structure, hinge 612c may be a living hinge, permitting pivoting of part 612a relative to part 612b. Piercing tip 608 may be made of any suitable biocompatible material, including bioresorbable materials or materials suitable for a permanent implant. It is contemplated that flange 612 may extend around a greater portion of the circumference of piercing tip 608 than is shown in the figures. For example, flange 612 may extend around a majority of the circumference of piercing tip 608, or multiple flanges 612 may extend around the circumference of piercing tip 608. When multiple flanges 612 are utilized, a majority of the circumference of piercing tip 608 may be encompassed by at least one of the flanges 612. Furthermore, while two parts (612a and 612b) and one hinge (612c) are shown, a given flange 612 may include additional parts and/or hinges. For example, one flange 612 may include three parts pivotable relative to one another by two hinges. These combinations are only exemplary. Other numbers of parts and flanges also are contemplated. In yet other embodiments, only a minority of the circumference of piercing tip 608 may be covered by a flange 612.

As shown in FIG. 36, piercing tip 608 is configured to have a first, insertion configuration suitable for insertion of piercing tip through the blood vessel wall. In that configuration, flange 612 assumes a bent profile, limiting the overall cross-sectional width of tip 608. In that profile, part 612a is pivoted relative to part 612b, and out of the plane of part 612b, Part 612a assumes a position aligned with the longitudinal axis of the lumen 613 of tip 608, and adjacent to the outer surface of the body of tip 608.

After insertion of tip 608 within the blood vessel, and pulling back of tip 608, part 612a will snag against the inner surface of the vessel wall, causing part 612a to pivot relative to part 612b and assume the second implanted configuration shown in FIGS. 34 and 35. Flange 612 may be configured so that part 612a cannot rotate past the plane of part 612b, for example by using a living hinge as hinge 612c. Flange 612, and particularly its proximal-facing surface, may include a tacky coating and/or bioadhesive to help maintain flange 612 against tissue.

Embodiments of the present disclosure may increase the speed of access into the neck for stroke treatments, and also speed up procedural times during other procedures, such as, e.g., femoral access. The angled shape of piercing tip 108 may allow for access into an artery (or other blood vessel) and provide a larger footprint for inside artery securement.

Although the exemplary embodiments described above have been disclosed in connection with medical devices for insertion into a blood vessel, those skilled in the art will understand that the principles set out above can be applied to any body lumen and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

What is claimed is:

1. A method for accessing and plugging a blood vessel of a subject using a medical device, the medical device including an outer assembly including a first shaft, a first lumen extending through the first shaft, and an atraumatic first tip removably coupled to a distal end of the first shaft, an inner assembly configured to extend through the first lumen of the outer assembly, the inner assembly including a second shaft, a second lumen extending through the second shaft, and a second tip removably coupled to a distal end of the second shaft, the second tip being configured to pierce tissue, and a plug assembly configured to extend through the second lumen of the inner assembly, the plug assembly including a third shaft and a plug removably coupled to a distal end of the third shaft, the method comprising:
   piercing a wall of the blood vessel using the second tip of the inner assembly of the medical device, thereby forming an opening in the blood vessel and positioning the inner assembly within the blood vessel;
   pulling the inner assembly proximally, so that second tip of the inner assembly abuts an inner surface of the wall of the blood vessel;
   pushing the outer assembly distally, so that the first tip of the outer assembly comes into contact with skin or an outer surface of the wall of the blood vessel, clamping the skin or the wall of the blood vessel with the second tip of the inner assembly;
   engaging the plug of the plug assembly with the second tip of the inner assembly to close the opening in the wall of the blood vessel;
   uncoupling the first tip from the first shaft, the second tip from the second shaft, and the plug from the third shaft, thereby plugging the opening of the wall of the blood vessel using the first tip, the second tip, and the plug; and
   pulling the first shaft, the second shaft, and the third shaft distally to remove them from the subject.

2. The method according to claim 1, wherein:
   the first tip includes a first tip lumen;
   the second tip extends through the first tip lumen; and
   the second tip includes a protrusion configured to engage with the first tip and secure the first tip to the second tip,
   wherein pushing the outer assembly distally includes engaging the protrusion of the second tip with the first tip.

3. The method according to claim 2, wherein the protrusion extends proximally from a proximal end of the second tip, and is configured to engage with a proximal end of the first tip via a snap-fit.

4. The method according to claim 1, wherein the first tip includes a first bevel at a distal end of the first tip.

5. The method according claim 4, wherein the second tip includes a second bevel configured to pierce tissue at a distal end of the second tip.

6. The method according to claim 5, wherein the inner assembly further includes a first flange that extends proximally from the second bevel at an angle offset from a longitudinal axis of the second tip.

7. The method according to claim 6, wherein the first flange includes a first part and a second part pivotable relative to the first part by a hinge.

8. The method according to claim 7, wherein:
   in a first configuration, the second part of the first flange extends at a first angle to the longitudinal axis of the second tip; and
   in a second configuration, the second part of the first flange extends at a second angle to the longitudinal axis of the second tip, wherein the second angle is different than the first angle.

9. The method according to claim 8, wherein pulling the inner assembly proximally causes the second part of the first flange to pivot from the first configuration to the second configuration.

10. The method according to claim 9, wherein the hinge is a living hinge.

11. The method according to claim 6, wherein the second tip includes:
   a second tip lumen extending through the second tip;
   an inner surface surrounding a distal portion of the second tip lumen; and
   a second flange extending radially inward from the inner surface and surrounding a proximal portion of the second tip lumen.

12. The method according to claim 11, wherein the plug:
   is a solid member without lumens;
   includes a bevel at a distal end; and
   includes a third flange extending circumferentially around a portion of the plug, wherein a distally-facing surface of the third flange is configured to abut a proximal-facing surface of the second flange when the plug is extended through the second lumen.

13. The method according to claim 1, wherein:
   the second tip includes a recess at a distal end of the second tip, the recess extending only partially around a circumference of the second tip; and the plug includes a protrusion configured to be received by the recess, the protrusion extending only partially around a circumference of the plug, wherein engaging the plug with the second tip includes receiving the protrusion of the plug within the recess of the second tip.

14. The method according to claim 1, wherein one or more of the first tip, the second tip, and the plug are bioresorbable.

15. The method according to claim 1, wherein each of the first tip, the second tip, and the plug are bioresorbable.

16. The method according to claim 1, wherein a diameter of the second shaft is less than a diameter of the first shaft.

17. The method according to claim 1, wherein the second tip further has a circumferential rim at a proximal end and a flange having a diameter that is less than a diameter of the circumferential rim.

18. A method for accessing and clamping a blood vessel of a subject using a medical device, the medical device including an outer assembly including a first shaft, a first lumen extending through the first shaft, and an atraumatic first tip removably coupled to a distal end of the first shaft, an inner assembly configured to extend through the first lumen of the outer assembly, the inner assembly including a second shaft, a second lumen extending through the second shaft, and a second tip removably coupled to a distal end of the second shaft, the second tip being configured to pierce tissue, and a plug assembly configured to extend through the second lumen of the inner assembly, the plug assembly including a third shaft and a plug removably coupled to a distal end of the third shaft, the method comprising:

piercing a wall of the blood vessel using the second tip of the inner assembly of the medical device, thereby forming an opening in the blood vessel and positioning the inner assembly within the blood vessel;

pulling the inner assembly proximally, so that second tip of the inner assembly abuts an inner surface of the wall of the blood vessel: and pushing the outer assembly distally, so that the first tip of the outer assembly comes into contact with skin or an outer surface of the wall of the blood vessel, thereby clamping the skin or the wall of the blood vessel with the second tip of the inner assembly.

19. A method for accessing and plugging a blood vessel of a subject using a medical device, the medical device including an outer assembly including a first shaft, a first lumen extending through the first shaft, and an atraumatic first tip removably coupled to a distal end of the first shaft and having a first bevel at a distal end thereof, an inner assembly configured to extend through the first lumen of the outer assembly, the inner assembly including a second shaft, a second lumen extending through the second shaft, and a second tip removably coupled to a distal end of the second shaft, the second tip having a second bevel at a distal end thereof, the second bevel being configured to pierce tissue, and a plug assembly configured to extend through the second lumen of the inner assembly, the plug assembly including a third shaft and a plug removably coupled to a distal end of the third shaft, the plug being a solid member without lumens and having a third bevel at a distal end thereof, the method comprising:

piercing a wall of the blood vessel using the bevel of the second tip of the inner assembly of the medical device, thereby forming an opening in the blood vessel and positioning the inner assembly within the blood vessel;

pulling the inner assembly proximally, so that second tip of the inner assembly abuts an inner surface of the wall of the blood vessel;

pushing the outer assembly distally, so that the first tip of the outer assembly comes into contact with skin or an outer surface of the wall of the blood vessel, clamping the skin or the wall of the blood vessel with the second tip of the inner assembly;

engaging the plug of the plug assembly with the second tip of the inner assembly to close the opening in the wall of the blood vessel;

uncoupling the first tip from the first shaft, the second tip from the second shaft, and the plug from the third shaft, thereby plugging the opening of the wall of the blood vessel using the first tip, the second tip, and the plug; and pulling the first shaft, the second shaft, and the third shaft distally to remove them from the subject.

* * * * *